US00RE44779E

(19) United States
(12) Reissued Patent
Imanishi et al.

(10) Patent Number: US RE44,779 E
(45) Date of Reissued Patent: Feb. 25, 2014

(54) BICYCLONUCLEOSIDE AND OLIGONUCLEOTIDE ANALOGUES

(75) Inventors: Takeshi Imanishi, Nara (JP); Satoshi Obika, Takatsuki (JP)

(73) Assignees: Santaris Pharma A/S, Hørsholm (DK); Exiqon A/S, Vedbaek (DK)

(21) Appl. No.: 13/533,781

(22) Filed: Jun. 26, 2012

Related U.S. Patent Documents

Reissue of:

(64) Patent No.: 6,268,490
Issued: Jul. 31, 2001
Appl. No.: 09/380,638
PCT Filed: Mar. 9, 1998
PCT No.: PCT/JP98/00945
§ 371 (c)(1),
(2), (4) Date: Sep. 7, 1999
PCT Pub. No.: WO98/39352
PCT Pub. Date: Sep. 11, 1998

(30) Foreign Application Priority Data

Mar. 7, 1997 (JP) ..... 9-53409

(51) Int. Cl.
*C07H 19/06* (2006.01)
*C07H 19/16* (2006.01)
*C07H 21/00* (2006.01)

(52) U.S. Cl.
CPC ..... *C07H 19/16* (2013.01); *C07H 19/06* (2013.01)
USPC ..... 536/23.1; 536/27.6; 536/28.54; 536/28.5; 536/26.7; 536/28.4; 536/26.9

(58) Field of Classification Search
None
See application file for complete search history.

(56) References Cited

U.S. PATENT DOCUMENTS

| | | | |
|---|---|---|---|
| 5,502,177 | A | 3/1996 | Matteucci et al. |
| 5,859,221 | A | 1/1999 | Cook et al. |
| 6,770,748 | B2 | 8/2004 | Imanishi et al. |
| 7,060,809 | B2 | 6/2006 | Wengel et al. |
| 7,084,125 | B2 | 8/2006 | Wengel |
| 2004/0014959 | A1 | 1/2004 | Sorensen et al. |

FOREIGN PATENT DOCUMENTS

| | | | |
|---|---|---|---|
| EP | 1 015 469 | A2 | 7/2000 |
| EP | 1 013 661 | B1 | 1/2012 |
| WO | WO 91/06556 | A1 | 5/1991 |
| WO | WO 92/03568 | A1 | 3/1992 |
| WO | WO 93/10820 | A1 | 6/1993 |
| WO | WO 94/24144 | A2 | 10/1994 |
| WO | WO 95/07918 | A2 | 3/1995 |
| WO | WO 97/47636 | A2 | 3/1995 |
| WO | 9747636 | * | 12/1997 |
| WO | WO 99/14226 | A2 | 3/1999 |
| WO | WO 03/039523 | A2 | 5/2003 |
| WO | WO 03/095467 | A1 | 11/2003 |
| WO | WO 2004/106356 | A1 | 12/2004 |
| WO | WO 2007/107162 | A2 | 9/2007 |
| WO | WO 2008/147824 | A2 | 12/2008 |
| WO | WO 2009/029862 | A2 | 4/2009 |

OTHER PUBLICATIONS

English translation of Nielsen, "Synthesis and incorporation of 4'-C-(hydroxymethyl) uridine in oligonucleotides", dissertation published Jan. 1995.*

Singh et al., "LNA (locked nucleic acids): synthesis and high-affinity nucleic acid recognition" Chemical Communications (1998) pp. 455-456.*

Koshkin et al., "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition" Tetrahedron (1998) vol. 54 pp. 3607-3630.*

Abe, F., et al., "Normonoterpenoids and Their Allopyranosides from the Leaves of *Cerbera* Species (Studies on *Cerbera*. VIII)," *Chem. Pharm. Bull.* 37:2639-2642, Pharmaceutical Society of Japan, Japan (1989).

Abe, F. and Yamauchi, T., "10-Carboyloganin, Normonoterpenoid Gluosides and Dinormonoterpenoid Glucosides from the Leaves of *Cerbera manghas* (Studies on *Cerbera*. 10)," *Chem. Pharm. Bull.* 44:1797-1800, Pharmaceutical Society of Japan, Japan (October 1996).

Beaucage, S. and Iyer, R., "Advances in the Synthesis of Oligonucleotides bythe Phosphoramidite Approach," *Tetrahedron* 48:2223-2311, Wiley-VCH Verlag GmbH & Co. KGaA, Germany (1992).

Brown, D. and Lin, P., "Synthesis and duplex stability of oligonucleotides containing adenine-guanine analogues," *Carbohydr. Res. 216*:129-139, Elsevier, Netherlands (1991).

Brown, D. and Lin, P., "The structure and application of oligodeoxyribonucleotides containing modified, degenerate bases," *Nucleic Acids Res. 24*:209-212, Oxford University Press, United Kingdom (1991).

Chaudhuri, N., et al., "C-Nucleosides Derived from Simple Aromatic Hydrocarbons," *Synlett 4*:341-347, Georg Thieme Verlag, Germany (Apr. 1997).

Cheson, B., "Perspectives on purine analogues," *Hematol. Cell Ther. 38*:S109-S116, Springer-Verlag, France (Dec. 1996).

Christensen, N., et al., "A Novel Class of Oligonucleotide Analogues Containing 2'-O,3'-C-Linked [3.2.0]Bicycloarabinonucleoside Monomers: Synthesis, Thermal Affinity Studies, and Molecular Modeling," *J. Am. Chem. Soc. 120*:5458-5463, American Chemical Society, United States (1998).

(Continued)

*Primary Examiner* — Eric S Olson
(74) *Attorney, Agent, or Firm* — Sterne, Kessler, Goldstein & Fox P.L.L.C.

(57) ABSTRACT

An oligo- or polynucleotide analogue having one or more structures of the general formula (I)

where B is a pyrimidine or purine nucleic acid base, or an analogue thereof, is disclosed. The use of this analogue provides an oligonucleotide analogue antisense molecule, which is minimally hydrolyzable with an enzyme in vivo, has a high sense strand binding ability, and is easily synthesized.

32 Claims, 2 Drawing Sheets

(56) References Cited

OTHER PUBLICATIONS

Daher, G., et al., "Metabolism Of Pyrimidine Analogues And Their Nucleosides," *Pharmacol. Ther. 48*:189-222, Pergamon Press PLC, United States (1990).

De Clercq, E. and Walker, R., "Synthesis And Antiviral Properties Of 5-Vinylpyrimidine Nucleoside Analogs," *Pharmacol. Ther. 26*:1-44, Pergamon Press Ltd., United States (1984).

Doronina, S. and Behr, J., "Towards a general triple helix mediated DNA recognition scheme," *Chem. Soc. Rev. 26*:63-71, Chemical Society, United Kingdom (Feb. 1997).

Ezzitouni, A. and Marquez, V., "Conformationally locked carocyclic nucleosides built on a bicyclo[3.1.0] hexane template with a fixed Southern conformation. Synthesis and antiviral activity," *J. Chem. Soc., Perkin Trans. 1*, pp. 1073-1078, RSC Publishing, United Kingdom (1997).

Freier, S. and Altman, K., "The ups and downs of nucleic acid duplex stability: structure-stability studies on chemically-modified DNA:RNA duplexes," *Nucleic Acids Res. 25*:4429-4443, Oxford University Press, United Kingdom (Nov. 1997).

Freier, S., "Hybridization properties of modified oligonucleotides," Presented at 1997 Gordon Conference, Jun. 29-Jul. 4, 1997, Colby-Sawyer College, New London, New Hampshire, United States.

Galán, E., et al., "Diels-Alder Reactions with an α,β-Unsaturated Aldehydo-sugar. A Route to 6-Oxabicyclo[3.2.1]octanes," *Tetrahedron Lett. 34*:1811-1814, Elsevier, United Kingdom (1993).

Gavrilyuk, O., et al., "Ciklizaciya aciklicheskih izoprenoidov VIII. Ciklizaciya geraniola, nerola i ih acetatov v syperkislotah" ("Cyclization of acyclic isoprenoids VIII. Cyclization of geraniol, nerol and their acetates in superacids"), *Zhurnal Organicheskoi Khimii 28*:1602-1614, Nauka (1992).

Griffey, R., et al., "Chapter 14: New Twists on Nucleic Acids: Structural Properties of Modified Nucleosides Incorporated into Oligonucleotides," in *Carbohydrate Modifications in Antisense Research,* Sanghvi, Y.S., and Cook, P.D., eds., pp. 212-224, Oxford University Press, United Kingdom (May 1994).

HÅkansson, A., et al., "Convenient syntheses of 7-hydroxy-1-(hydroxymethyl)-3-(thymin-1-yl)-2,5-dioxabicyclo," *J. Org. Chem. 65*:5161-5166, American Chemical Society, United States (Aug. 2000).

Herdewijn, P., "Targeting RNA with Conformationally Restricted Oligonucleotides," *Liebigs Ann. 1996*: 1337-1348, Verlag Chemie, Germany (Sep. 1996).

Hirota, K., et al., "Simple Method for the Synthesis of 5-Substituted 2',5'-Anhydro-2',5'-dideoxy-1-β-$_D$-arabinofuranosyluracils," *J. Chem. Soc. Chem. Commun.,* pp. 108-109, Royal Society of Chemistry, United Kingdom (1984).

Hrdlicka, P., et al., "Synthesis and biological evaluation of branched and conformationally restricted analogs of the anticancer compounds 3'-C-ethynyluridine and 3'-C-ethynylcytidine (ECyd)," *Bioorg. Med. Chem. 13*:2597-2621, Elsevier Science, United Kingdom (Apr. 2005).

Hrdlicka, P., et al., "Synthesis and biological evaluation of conformationally restricted and nucleobase-modified analogs of the anticancer compound 3'-C-ethynylcytidine (ECyd)," *Nucleosides Nucleotides Nucleic Acids 24*:397-400, Marcel Dekker, New York, New York, United States (Jan. 2005).

Kawasaki, A., et al., "Synthesis And Biophysical Studies Of 2'-dRibo-2'-F Modified Oligonuclotides," Presentation, Isis Pharmaceuticals, Jan. 1991, 10 pages.

Koshkin, A., et al., "LNA (Locked Nucleic Acid): An RNA Mimic Forming Exceedingly Stable LNA:LNA Duplexes," *J. Am. Chem. Soc. 120*:13252-13253, American Chemical Society, United States (Dec. 1998).

Koshkin, A., et al., "LNA (Locked Nucleic Acids): Synthesis of the Adenine, Cytosine, Guanine, 5-methylcytosine, Thymine and Uracil Bicyclonucleoside Monomers, Oligomer-isation, and Unprecedented Nucleic Acid Recognition," *Tetrahedron 54*:3607-3630, Pergamon Press, United Kingdom (1998).

Koshkin, A., et al., "Novel Convenient Synthesis of LNA [2.2.1]Bicyclo Nucleosides," *Tetrahedron Lett. 39*:4381-4384, Elsevier, United Kingdom (Jun. 1998).

Koshkin, A. and Wengel, J., "Synthesis of Novel 2',3'-Linked Bicyclic Thymine Ribonucleosides," *J. Org. Chem. 63*:2778-2781, American Chemical Society, United States (1998).

Kulikowski, T., "Structure-activity relationships and conformational features of antiherpetic pyrimidine and purine nucleoside analogues. A review," *Pharm. World Sci. 16*:127-138, Springer, Germany (1994).

Lee, C., et al., "Synthesis And Reactions Of 3-C-Branched-Chain Analogues of 3,6-Anhydrodeoxynojirimycin," *J. Carbohydr. Chem. 16*:49-62, Marcel Dekker, Inc., United States (Jan. 1997).

Lehmann, T., et al., "136. Triple-Helix Formation by Pyrimidine Oligonucleotides Containing Nonnatural Nucleosides with Extended Aromatic Nucleobases: Intercalation from the Major Groove as a Method for Recognizing C•G and T•A Base Pairs," *Helvetica Chimica Acta 80*:2002-2022, Verlag Helvetica Chimica Acta, Germany (Sep. 1997).

Luyten, I. and Herdewijn, P., "Hybridization properties of base-modified oligonucleotides within the double and triple helix motif," *Eur. J Med. Chem. 33*:515-576, Elsevier, France (Jul.-Aug. 1998).

Madsen, A., et al., "Synthesis, nucleic acid hybridization properties and molecular modelling studies of conformationally restricted 3'-O,4'-C-methylene-linked α-L-ribonucleotides," *Carbohydr. Res. 341*:1398-1407, Elsevier, Netherlands (Jul. 2006).

Mazumder, A., et al., "Effects of Nucleotide Analogues on Human Immunodeficiency Virus Type 1 Integrase," *Mol. Pharmacol. 49*:621-628, American Society for Pharmacology and Experimental Therapeutics, United States (Apr. 1996).

Meldgaard, M. and Wengel, J., "Bicyclic nucleosides and conformational restriction of oligonucleotides," *J. Chem. Soc. Perkin Trans. 1 21*:3539-3554, Royal Society of Chemistry, United Kingdom (Nov. 2000).

Milligan, J., et al., "Current Concepts in Antisense Drug Design," *J. Med. Chem. 36*:1923-1937, American Chemical Society, United States (1993).

Moore, M., et al., "Direct Observation of Two Base-pairing Models of a Cytosine-Thymine Analogue with Guanine in a DNA Z-form Duplex: Significance for Base Analogue Mutagenesis," *J. Mol. Biol. 251*:665-673, Academic Press Limited, United States (1995) (Abstract Only).

Negishi, K., et al., "Nucleoside and nucleobase analog mutagens," *Mutat. Res. 318*:227-238, Elsevier, Netherlands (1994).

Nielsen, P. and Wengel, J., "Synthesis and chemoselective activation of phenyl 3,5-di-O-benzyl-2-O,4-C-methylene-1-thio-β-$_D$-ribofuranoside: a key synthon towards α-LNA," *Chem. Commun. (Camb.)* 23:2645-2646, Royal Society of Chemistry, United Kingdom (Dec. 1998).

Certified English translation by Luann Cheney-Smith, Merrill Brink International, U.S. (2008) of Nielsen, K., "Synthesis and Incorporation of 4'-C-(hydroxymethyl) Uridine in Oligonucleotides," Master's thesis, *Department of Chemistry—Odense University*, Odense, Denmark (Jan. 1995).

Nielsen, P., et al., "Synthesis of 2'-O,3'-C-linked bicyclic nucleosides and bicyclic oligonucleotides," *J. Chem. Soc., Perkin Trans. 1,* pp. 3423-3434, RSC Publishing, United Kingdom (1997).

Obika, et al., "Synthesis and Properties of Oligonucleotides containing novel bicyclic nucleosides with a fixed N-form sugar puckering," Poster Session, Poster No(s). P-32 and P-33, Program for the 7$^{th}$ Antisense Symposium Program, Nov. 21-22, 1997, 8 pages.

Ørum, H., and Wengel, J., "Locked nucleic acids: a promising molecular family for gene-function analysis and antisense drug development," *Curr. Opin. Mol. Ther. 3*:239-243, Thomson Reuters, United Kingdom (Jun. 2001).

Plunkett, W. and Gandhi, V., "Pharmacology of purine nucleoside analogues," *Hematol. Cell Ther. 38*:S67-S74, Springer-Verlag, Germany (Dec. 1996).

Polovinka, M., et al., "Novii Pyt' Sinteza bisiclicheskih Prostih Efirov Iz Terpenoidnih Spirtov Karanovogo i Mentanovogo Ryadov" ("New Synthetic Route for Bicyclic Simple Ethers from Terpenoid Alcohols of Carane and Menthane Series," *Zhurnal Organicheskoi Khimii 28*:2253-2267, Nauka (1992).

(56) References Cited

OTHER PUBLICATIONS

Rajwanshi, V., et al., "Synthesis and restricted furanose conformations of three novel bicyclic thymine nucleosides: a *xylo*-LNA nucleoside, a 3'-O,5'-C-methylene-linked nucleoside, and a 2'-O,5'-C-methylene-linked nucleoside," *J. Chem. Soc. Perkin Trans. 1 11*:1407-1414, Royal Society of Chemistry, United Kingdom (Jun. 1999).
Ruiz-Perez, C., et al., "Structure of 5-Hydroxymethyl-7,7-dimethyl-6-oxabicylo[3.2.1]octane-1-carboxylic Acid," *Acta Crystallogr. C46*:1507-1509, International Union of Crystallography, United Kingdom (1990).
Shibahara, S., et al., "Site-directed cleavage of RNA," *Nucleic Acids Res. 15*:4403-4415, Oxford University Press, United Kingdom (1987).
Singh, S. and Wengel, J., "University of LNA-mediated High-affinity Nucleic Acid Recognition," *Chem. Comm.,* pp. 1247-1248, Royal Society of Chemistry, United Kingdom (Jun. 1996).
Singh, S., et al, "Synthesis of 2'-amino-LNA:A novel conformationally restricted high-affinity oligonucleotide analogue with a handle," *J. Org. Chem. 63*:10035-10039, American Chemical Society, United States (Dec. 1998).
Singh, S., et al., "Synthesis of Novel Bicyclo[2.2.1] Ribonucleosides: 2'Amino- and 2'-Thio-LNA Monomeric Nucleosides," *J. Org. Chem. 63*:6078-6079, American Chemical Society, United States (Sep. 1998).
Sørensen, M., et al., "α-L-ribo-Configured locked nucleic acid (αL-LNA): Synthesis and properties," *J. Am. Chem. Soc. 124*:2164-2176, American Chemical Society, United States (Mar. 2002).
Stoeckler, J., et al., "Design of purine nucleoside phosphorylase inhibitors," *Fed. Proc. 45*:2773-2778, Federation Of American Societies For Experimental Biology, United States (1986).
Tino, J., et al., "Synthesis And Antiviral Activity Of Novel Isonucleoside Analogs," *J. Med. Chem. 36*:1221-1229, American Chemical Society, United States (1993).
Uhlmann, E. and Peyman, A., "Antisense Oligonucleotides: A New Therapeutic Principle," *Chem. Rev. 90*:544-584, American Chemical Society, United States (1990).
Van Aerschot, A., et al., "An acyclic 5-nitroindazole nucleoside analogue as ambiguous nucleoside," *Nucleic Acids Res. 23*:4363-4370, Oxford University Press, United Kingdom (1995) (Abstract only).
Wagner, R., "Antisense Gene Inhibition by Oligonucleotides Containing C-5 Propyne Pyrimidines," *Science 260*:1510-1513, American Association for the Advancement of Science, United States (1993).
Wengel, J., "Synthesis of 3'-C- and 4'-C-Branched Oligodeoxynucleotides and the Development of Locked Nucleic Acids (LNA)," *Acc. Chem. Res. 32*:301-310, American Chemical Society, United States (Apr. 1999).
Wengel, J., et al., "Chemistry of Locked Nucleic Acids (LNA): Design, Synthesis, and Biophysical Properties," *Lett. Pept. Sci. 10*:237-253, Kluwer Academic Publishers, Netherlands (2004).
Wengel, J., "LNA (Locked Nucleic Acids): Synthesis and high-affinity nucleic acid recognition—Stop the twisting!," National Seminar on Perspectives in Interfacial Areas of Chemistry and Biology, Department of Chemistry, Delhi University, New Delhi, India, Jan. 20-22, 1998, 38 pages.
Wood, S., et al., "Guanine and adenine analogues as tools in the investigation of the mechanisms of mismatch repair in *E. coli," Nucleic Acids Res. 14*:6591-6602, Oxford University Press, United Kingdom (1986) (Abstract only).
Yannopoulos, C., et al., "2'3'-Cyclopropanated Nucleoside Dimers," *Synlett:*378-380, Georg Thieme Verlag, Germany (1997).
Youssefyeh, R., et al., "4'-Substituted Nucleosides. 4. Synthesis of Some 4'-Hydroxymethyl Nucleosides," *J. Org. Chem. 44*:1301-1309, American Chemical Society, United States (1979).
Zigeuner, G. and Wendelin, W., "Heterocycles. XVI. 1,4-Dimethyl-3-acetoxy-7-acetamido-2-oxabicyclo[2.2.1]heptane," *Chemical Abstracts 70*:343, Abstract No. 3737b, American Chemical Society, United States (1969).
Observations by Third Parties for European Patent Application No. 98905804.5, Exiqon A/S, dated Dec. 20, 2000, 2 pages.
Obika, S., et al., "Synthesis of 2'-O,4'-C-Methyleneuridine and -cytidine. Novel Bicyclic Nucleosides Having a Fixed $C_3$-endo Sugar Puckering," *Tetrahedron Lett. 38*:8735-8738, Elsevier, Netherlands (Dec. 1997).
Altmann, K-H., et al., "6'-Carbon-Substituted Carbocyclic Analogs of 2'-Deoxyribonucleosides-Synthesis and Effect on DNA/RNA Duplex Stability," *Tetrahedron* 52(39):12699-12722, Elsevier Science Ltd., England (1996).
Beaucage, S.L., "Oligonucleotide Synthesis—Phosphoramidite Approach," in *Methods in Molecular Biology, vol. 20: Protocols for Oligonucleotide and Analogs*, S. Agrawal (ed.), pp. 33-61, Humana Press Inc., United States (1993).
Beaucage S.L. and Iyer, R.P., "The Synthesis of Modified Oligonucleotides by the Phosphoramidite Approach and Their Applications," *Tetrahedron 49*(28):6123-6194, Pergamon Press, Ltd., England (1993).
Lehninger, A.L., et al., *Principle of Biochemistry,* Second Edition, pp. 324-327, Worth Publishers, United States (1993).
Sanghvi, Y.S., "Heterocyclic Base Modifications in Nucleic Acids and Their Applications in Antisense Oligonuceotides," in *Antisense Research and Applications*, pp. 273-288, Crooke & LeBleu (eds.), CRC Press, United States (1993).
Altmann, K.-H., et al., "4',6'-Methano Carbocyclic Thymidine: A Conformationally Constrained Building Block for Oligonucleotides," *Tetrahedron Letters 35(15)*: 2331-2334, Elsevier Science Ltd., Great Britain (1994).
Declaration of Punit P. Seth, Ph.D., Mar. 25, 2009, filed on behalf of Isis Pharmaceuticals, Inc. In the Inter Partes Reexamination of U.S. Patent No. 6,770,748, Control No. 95/001,076.
Declaration of Emmanuel A. Theodorakis, Ph.D., Mar. 26, 2009, filed on behalf of Isis Pharmaceuticals, Inc. in the Inter Partes Reexamination of U.S. Patent No. 6,770,748, Control No. 95/001,076.
Declaration of Bjarne Christensen, Dec. 16, 2009, filed on behalf of Patent Owners in the Inter Partes Reexamination of U.S. Patent No. 6,770,748, Control No. 95/001,076.
Imanishi, T., et al., "Synthesis and Property of Novel Conformationally Constrained Nucleoside and Oligonucleotide Analogs," abstract for *The Sixteenth International Congress of Heterocyclic Chemistry* (Aug. 1997).
Research laboratory notebook pages attributed to Punit P. Seth, Ph.D., 48 pages, dated Jun. 30 to Jul. 28, 2008.
Research laboratory notebook pages attributed to Emmanuel A. Theodorakis, Ph.D., 110 pages, dated Jan. 23 to Feb. 18, 2009.
Notice of Opposition of European Patent No. 1 013 661 B1, filed on Oct. 18, 2012, by Isis Pharmaceuticals, Inc.
Obika, S., et al.,"Synthesis and conformation of 3'-O,4'-C-methyleneribonucleosides, novel bicyclic nucleoside analogues for 2',5'-linked oligonucleotide modification," *Chem. Commun. 17*:P1643-1644, Royal Society of Chemistry, United Kingdom (1997).
Second Declaration of Punit P. Seth, Ph.D., Jan. 19, 2010, filed on behalf of Isis Pharmaceuticals, Inc. in the Inter Partes Reexamination of U.S. Patent No. 6,770,748, Control No. 95/001,076.
Second Declaration of Emmanuel A. Theodorakis, Ph.D., Jan. 20, 2010, filed on behalf of Isis Pharmaceuticals, Inc. in the Inter Partes Reexamination of U.S. Patent No. 6,770,748, Control No. 95/001,076.
Declaration of Karl-Heinz Altmann, Ph.D., Jan. 20, 2010, filed on behalf of Isis Pharmaceuticals, Inc. in the Inter Partes Reexamination of U.S. Patent No. 6,770,748, Control No. 95/001,076.
Declaration of Heinz E. Moser, Ph.D., Jan. 18, 2010, filed on behalf of Isis Pharmaceuticals, Inc. in the Inter Partes Reexamination of U.S. Patent No. 6,770,748, Control No. 95/001,076.
Declaration of K.C. Nicolaou, Ph.D., Jan. 20, 2010, filed on behalf of Isis Pharmaceuticals, Inc. in the Inter Partes Reexamination of U.S. Patent No. 6,770,748, Control No. 95/001,076.
Beaucage††, "Oligonucleotide Synthesis—Phosphoramidite Approach," Ch. 3 in *Methods in Molecular Biology, vol. 20: Protocols for Oligonucleotide and Analogues*, S. Agrawal (ed.), 1993, Humana Press, Totowa, NJ, pp. 33-61.*

(56) References Cited

OTHER PUBLICATIONS

Beaucage et al. (I)††, "Advances in the Synthesis of Oligonucleotides by the Phosphoramidite Approach," (Tetrahedron Report No. 309) *Tetrahedron, 48*(12), 2223-2311 (1992).*
Beaucage et al. (II)\\, "The Synthesis of Modified Oligonucleotides by the Phosphoramidite Approach and Their Applications," *Tetrahedron,49*(28), 6123-6194 (1993).*
Lehninger et al.\\, *Principle of Biochemistry, Second Edition,* Worth Publishers, 1993, only pp. 324-327 supplied.*
Sanghvi\\, "Heterocyclic Base Modifications in Nucleic Acids and Their Applications in Antisense Oligonuceotides," Ch. 15 in *Antisense Research and Applications,* Crooke & LeBleu (eds.), CRC Press, Boca Raton, FL, 1993, pp. 273-288.*
Obika et al., "Synthesis of 2'-o, 4'-C-Methyleneuridine and -cytidine. Novel Bicyclic Nucleosides Having a Fixed $C_3$, -endo Sugar Puckering," *Tetrahedron Letters, 38*(50), 8735-8738 (Dec. 15, 1997).*
Altmann et al., "6'-Carbon-Substituted Carbocyclic Analogs of 2'-Deoxyribonucleosides—Synthesis and Effect on DNA/RNA Duplex Stability," *Tetrahedron,* 52(39), 12699-12722 (1996).*
Nielsen et al., "Synthesis and Chemoselective Activation of Phenyl 3, 5-Di-o-benzyl-2-o, 4-C-methylene-1-thio-β-D-ribofuranoside: A Key Synthon Towards α-LNA," *Chemical Communications,* (Issue No. 23), 2645-2646 (Dec. 7, 1998).*
Herdewijn, "Targeting RNA with Conformationally Restricted Oligonucleotides," *Liebigs Annalen,* (Issue No. 9), 1337-1348 (Sep. 1996).*
Sanjay Singh et al., "LNA (locked Nucleic Acids):Synthesis and High-Affinity Nucleic Acid Recognition", Chemical Communications, Royal Society of Chemistry, GB, No. 4, pp. 455-456, Feb. 21, 1998.

* cited by examiner

BICYCLONUCLEOSIDE AND OLIGONUCLEOTIDE ANALOGUES

Matter enclosed in heavy brackets [ ] appears in the original patent but forms no part of this reissue specification; matter printed in italics indicates the additions made by reissue.

CROSS REFERENCE TO RELATED APPLICATION

The present application is the national stage under 35 U.S.C. 371 of PCT/JP98/00945, filed Mar. 9, 1998.

TECHNICAL FIELD

This invention relates to a novel nucleoside analogue and a novel nucleotide analogue, and more particularly, to a nucleotide analogue suitable as an antisense molecule.

BACKGROUND ART

In 1978, it was reported for the first time that an antisense molecule inhibited influenza virus infection. Since then, reports have been issued that antisense molecules inhibited the expression of oncogenes and AIDS infection. In recent years, antisense oligonucleotides have become one of the most promising pharmaceuticals, because they specifically control the expression of undesirable genes.

The antisense method is based on the idea of controlling a unidirectional flow called the central dogma, i.e., DNA→RNA→protein, by use of an antisense oligonucleotide.

When a naturally occurring oligonucleotide was applied to this method as an antisense molecule, however, it was decomposed with various nucleases in vivo, or its permeation through the cell membrane was not high. To solve these problems, numerous nucleic acid derivatives and analogues have been synthesized, and their studies have been conducted. Examples of the synthesized products include a phosphorothioate having a sulfur atom substituting for an oxygen atom on the phosphorus atom, and a methylphosphonate having a substituting methyl group. Recently, products have been synthesized in which the phosphorus atom has also been substituted by a carbon atom, or the structure of the sugar portion has been changed, or the nucleic acid base has been modified. Any resulting derivatives or analogues, however, have not been fully satisfactory in terms of In vivo stability, ease of synthesis, and sequence specificity (the property of selectively controlling the expression of a particular gene alone).

Under these circumstances, the re has been a demand for the creation of an antisense molecule which is minimally decomposed with a nuclease in vivo, binds to target messenger RNA with high affinity, has high specificity, and can thus efficiently control the expression of a particular gene.

DISCLOSURE OF THE INVENTION

The Inventors of the present invention designed a nucleic acid analogue with immobilized conformation of the sugar portion in a nucleic acid, which would be useful in the antisense method. They synthesized a nucleoside analogue which will be a unit structure therefor, and confirmed that an oligonucleotide analogue prepared using it was very useful as an antisense molecule.

Figure 1:
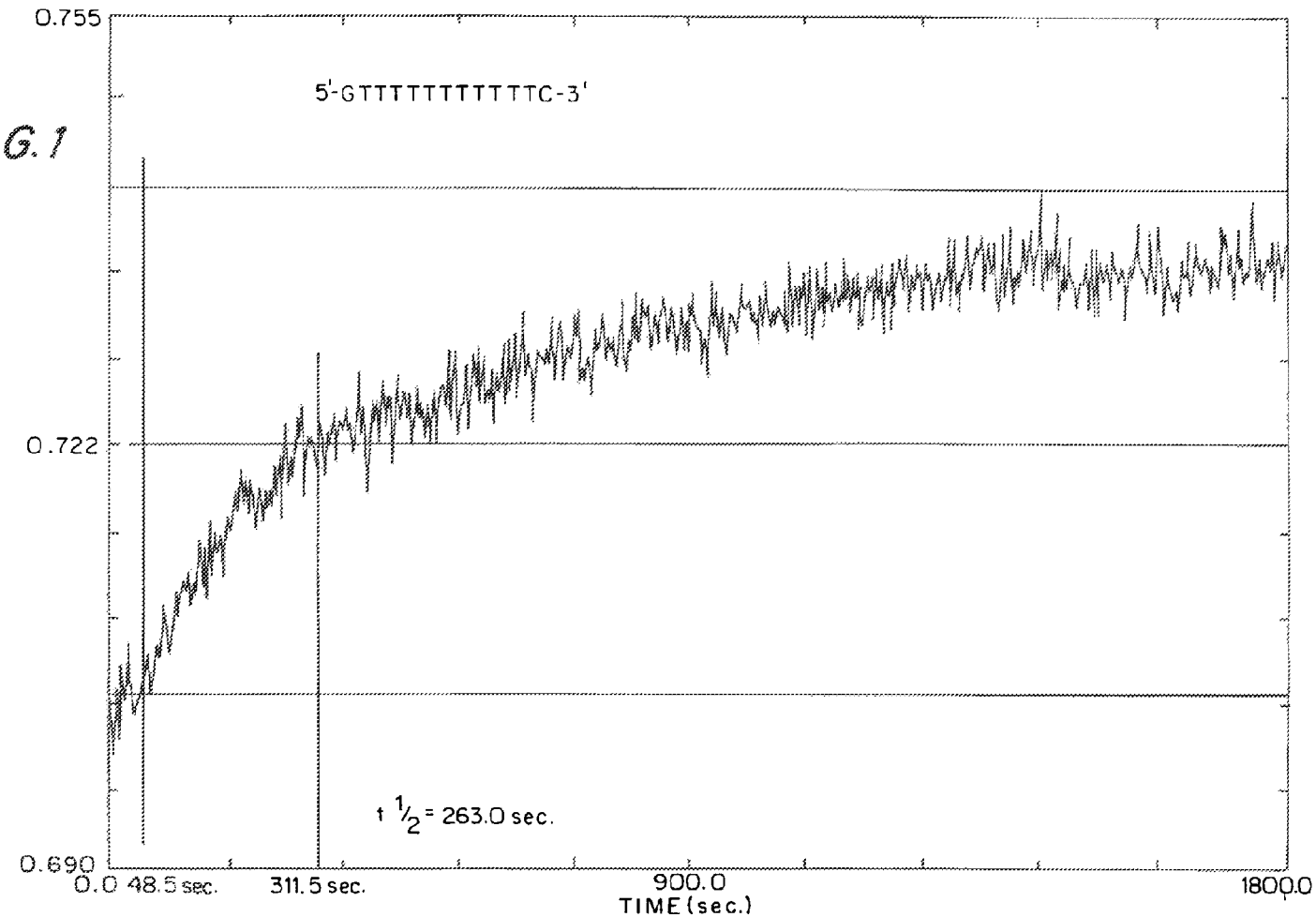
FIG. 1 is a chart showing the time course of the ultraviolet absorption (260 nm) of a naturally occurring oligonucleotide decomposed with an exonuclease.

Details of the present invention will now be described.

The structure of a nucleoside analogue according to the present invention is a nucleoside analogue of the following general formula (I)

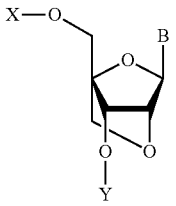

(I)

where B is a pyrimidine or purine nucleic acid base, or an analogue thereof, and X and Y are identical or different, and each represents a hydrogen atom, and alkyl group, an alkenyl group, an alkynyl group, a cycloalkyl group, an aralkyl group, an aryl group, an acyl group, or a silyl group, or an amidite derivative thereof.

The alkyl group represents a straight chain or branched chain alkyl group with 1 to 20 carbon atoms. Its examples include methyl, ethyl, n-propyl, i-propyl, n-butyl, t-butyl, pentyl, hexyl, heptyl, octyl, nonyl and decyl.

The alkenyl group represents a straight chain or branched chain alkenyl group with 2 to 20 carbon atoms. Its examples include vinyl, allyl, butenyl, pentenyl, geranyl, and farnesyl.

The alkynyl group represents a straight chain or branched chain alkynyl group with 2 to 20 carbon atoms. Its examples include ethynyl, propynyl, and butynyl.

The cycloalkyl group represents a cycloalkyl group with 3 to 8 carbon atoms, and includes, for example, cyclopropyl, cyclobutyl, cyclopentyl, cyclohexyl, cycloheptyl, and cyclooctyl. Another example is a heterocyclic group in which one or more arbitrary methylene groups on the ring of the cycloalkyl group have been substituted by an oxygen atom, a sulfur atom, or an alkyl-substituted nitrogen atom. It Is, for instance, a tetrahydropyranyl group.

The aryl group refers to a monovalent substituent formed by removing one hydrogen atom from an aromatic heterocyclic group or an aromatic hydrocarbon group. Preferably, it represents a monovalent substituent formed by removing one hydrogen atom from an aromatic hydrocarbon group, and includes, for example, phenyl, tolyl, xylyl, biphenyl, naphthyl, anthryl, and phenanthryl. The carbon atom on the ring of the aryl group may be substituted by one or more of a halogen atom, a lower alkyl group, a hydroxyl group, an alkoxy group, an amino group, a nitro group, a trifluoromethyl group or an aryloxy group.

The aralkyl group refers to an alkyl group bonded to an aryl group, and may be substituted. The aralkyl group that may be substituted represents an alkyl group bonded to an aryl group, with one or more arbitrary hydrogen atoms of the aryl group and the alkyl group being optionally substituted by the following substituents: Examples of the substituents are acyl, amino, aryl, alkyl, cycloalkyl, alkoxy, hydroxyl, nitro, and halogen.

The amino group need not be substituted, but the amino group when substituted includes, for example, alkylamino, arylamino, and acylamino. Examples of the alkoxy group are methoxy, ethoxy, n-propoxy, i-propoxy, n-butoxy, i-butoxy, s-butoxy, t-butoxy, pentyloxy, hexyloxy, and phenoxy. Examples of the halogen atom are fluorine, chlorine, bromine, and iodine.

The preferred examples of the aralkyl group are trityl, benzyl, phenethyl, tritylmethyl, diphenylmethyl, naphthylmethyl, and 4,4'-dimethoxytrityl (DMTr). Particularly preferred is a DMTr group.

As the acyl group, acetyl, formyl, propionyl, benzoyl, and benzyloxycarbonyl can be exemplified. An example of the silyl group is a trialkylsilyl group, preferably trimethylsilyl, triethylsilyl, triisopropylsilyl, t-butyldimethylsilyl or t-butyldiphenylsilyl, and more preferably trimethylsilyl.

The nucleotide analogue of the present invention is an oligonucleotide or polynucleotide analogue having one or more structures of the general formula (Ia)

(1a)

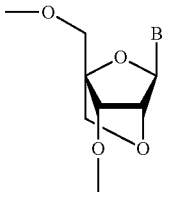

where B is a pyrimidine or purine nucleic acid base, or an analogue thereof, or an oligonucleotide or polynucleotide analogue of the general formula (II)

(II)

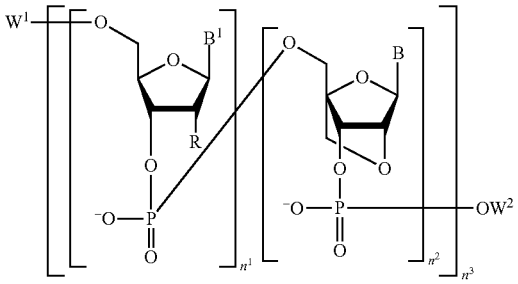

where $B^1$ and B are identical or different, and each represents a pyrimidine or purine nucleic acid base, or an analogue thereof, R is a hydrogen atom, a hydroxyl group, a halogen atom, or an alkoxy group, $W^1$ and $W^2$ are identical or different, and each represents a hydrogen atom, an alkyl group, an alkenyl group, an alkynyl group, a cycloalkyl group, an aralkyl group, an aryl group, an acyl group, a silyl group, a phosphoric acid residue, a naturally occurring nucleoside or a synthetic nucleoside bound via a phosphodiester bond, or an oligonucleotide or polynucleotide containing the nucleoside, $n^1$'s or $n^2$'s are identical or different, and each denote an integer of 0 to 50, provided that $n^1$'s or $n^2$'s are not zero at the same time, and that not all of $n^2$'s are zero at the same time, $n^3$ denotes an integer of 1 to 50, provided that when $n^1$ and/or $n^2$ are or is 2 or more, $B^1$ and B need not be identical, and R's need not be identical.

The pyrimidine or purine nucleic acid base in the present invention refers to thymine, uracil, cytosine, adenine, guanine, or a derivative thereof.

The nucleoside analogue and nucleotide analogue of the present invention can be synthesized in the manner described below.

(1) Synthesis of nucleoside analogue

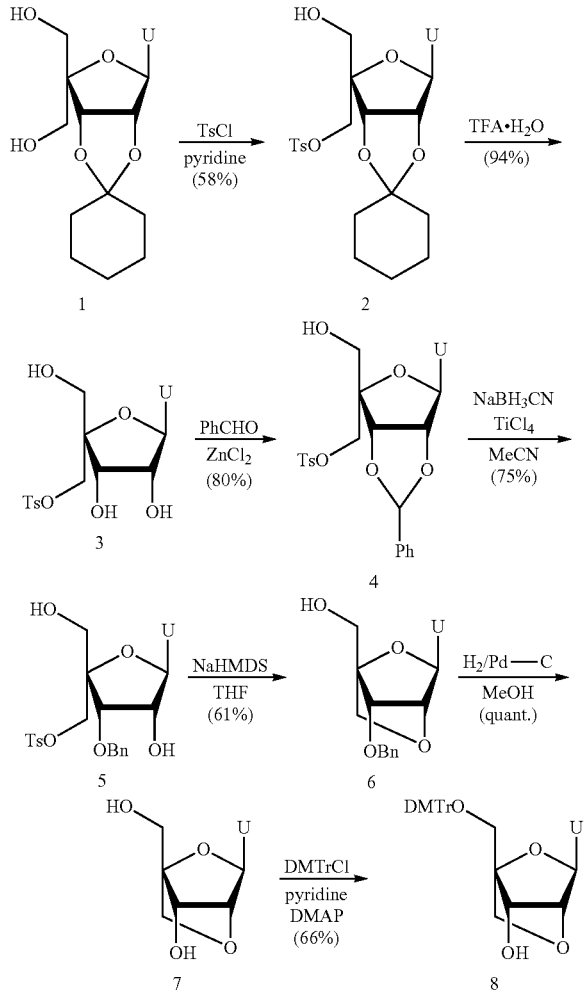

Compound 1, synthesized from uridine in accordance with the literature [1) J. A. Secrist et al., J. Am. Chem. Soc., 101, 1554 (1979); 2) G. H. Jones et al., J. Org. Chem., 44, 1309 (1979)], was treated with tosyl chloride (TsCl) to tosylate only one of the two primary alcohols, leading to Compound 2. Compound 2 was acid hydrolyzed into a triol compound 3. Compound 3 was condensed with benzaldehyde in the presence of an acid catalyst to form a benzylidene compound 4. Compound 4 was reduced with sodium cyanoborohydride ($NaBH_3CN$) in the presence of titanium tetrachloride ($TiCl_4$) to obtain Compound 5. This compound was reacted with sodium hexamethyldisilazide (NaHMDS) in tetrahydrofuran (THF) to obtain a bicyclo compound 6 (Compound I: B=uracil (U), X=H, Y=benzyl). When Compound 6 was catalytically reduced in the presence of a palladium carbon catalyst, a diol compound 7 (Compound (I): B=U, X=Y=H) was obtained. Further treatment of Compound 7 with 4,4'-dimethoxytrityl chloride (DMTrCl) gave a trityl compound 8

(Compound I: B=U, X=DMTr, Y=H). Compounds 6, 7 and 8 can be used as starting materials for various compounds I.

Compounds (I) having various nucleic acid bases, whether natural or nonnatural, other than uridine, can be synthesized by any of the following three methods:

The first method is conversion from Compound 8. That is, Compound 8 is acetylated into Compound 9, and then reacted with 1,2,4-triazole to form Compound 10. Hydrolysis of this compound gave Compound 11 (Compound (I): B=cytosine (C), X=DMTr, Y=H). Compound 12 (Compound (I): B=benzoylcytosine ($C^{Bz}$), X=DMTr, Y=H), which will become a starting material for oligonucleotide synthesis, can be easily obtained by benzoylation of Compound 11.

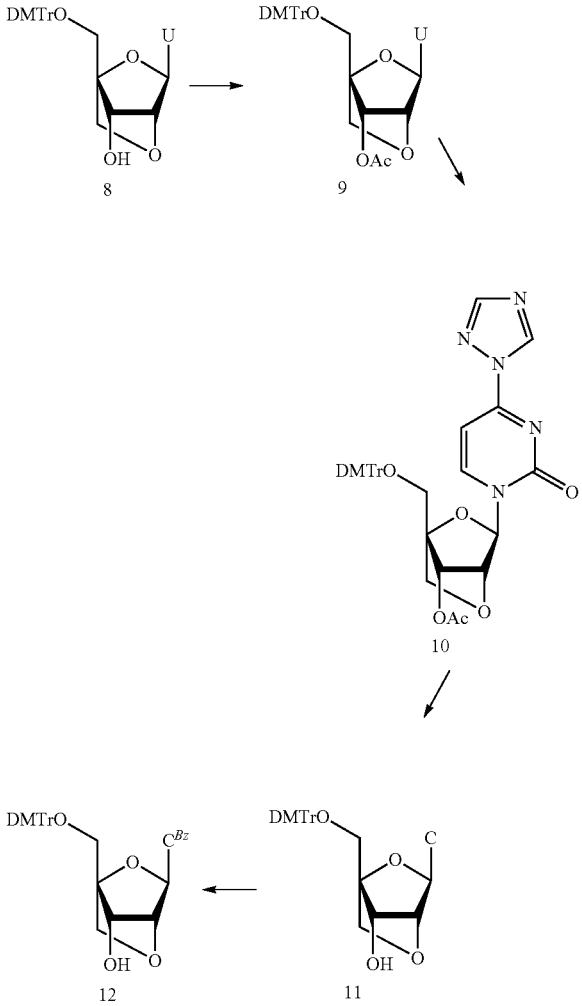

The second method is a method performed via Compound 13 which can be easily obtained from D-ribose in accordance with the literature [3) A. G. M. Barrett et al., J. Org. Chem., 55, 3853 (1990); 4) G. H. Jones et al., ibid., 44, 1309 (1979)]. That is, Compound 13 was led to Compound 16 by three steps, and cyclized under basic conditions to obtain a desired methylglycosyl compound 17. The OMe group at the 1-position of this compound can be substituted by different natural nucleic acid bases or nonnatural nucleic acid base analogues by various methods which have already been developed. For example, a method as shown by a scheme ranging from Compound 17 to Compound 20 can be employed.

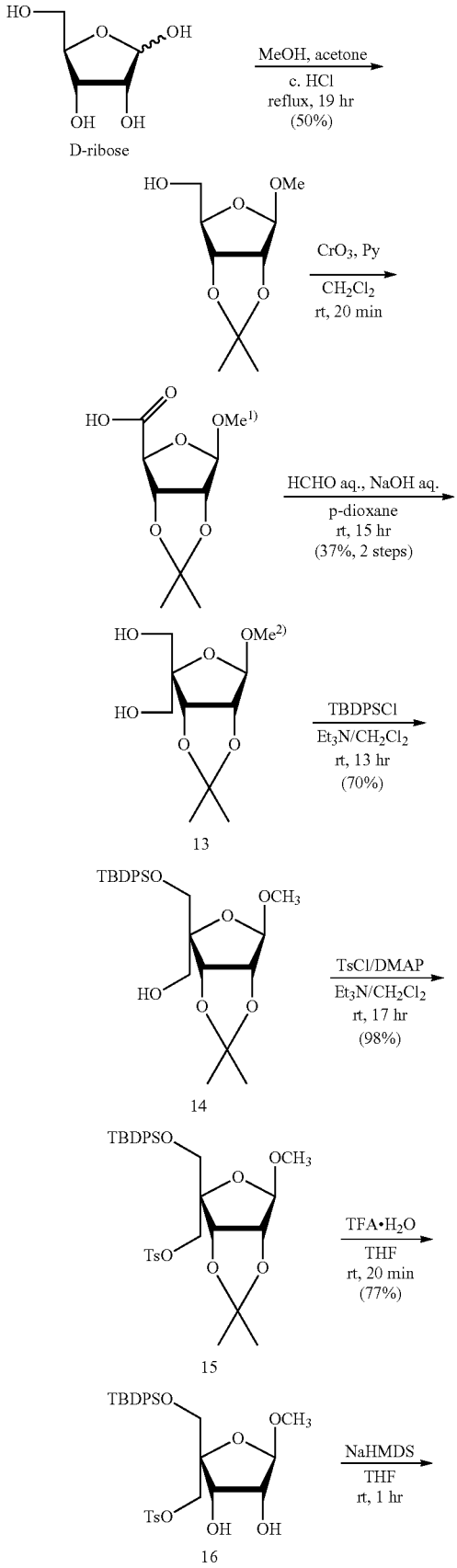

-continued

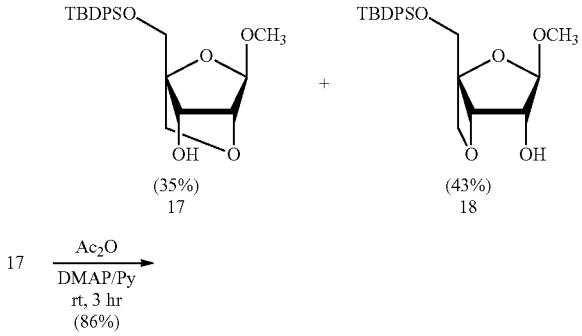

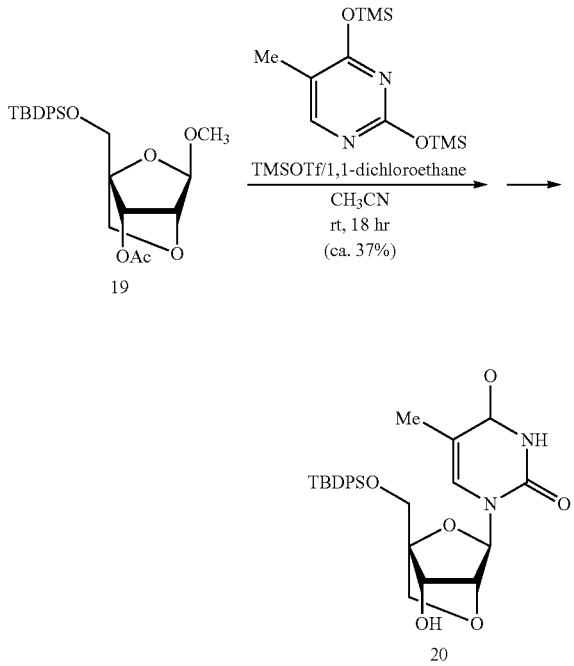

The third method starts with diacetone D-glucose, which is obtained from D-glucose by one step and is commercially available. Compound 31 was prepared in accordance with a reference 5) R. D. Youssefyeh, J. P. H. Verheyden and J. G. Moffatt., J. Org. Chem., 44, 1301-1309 (1979). Then, Compound 31 was treated as shown by the following scheme to protect the two primary hydroxyl groups with a t-butyldiphenylsilyl group and a p-toluenesulfonyl group progressively. The protected compound was acetylated into Compound 34.

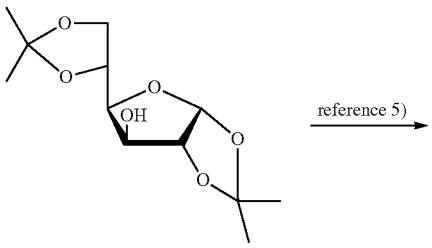

Diacetone D-glucose

-continued

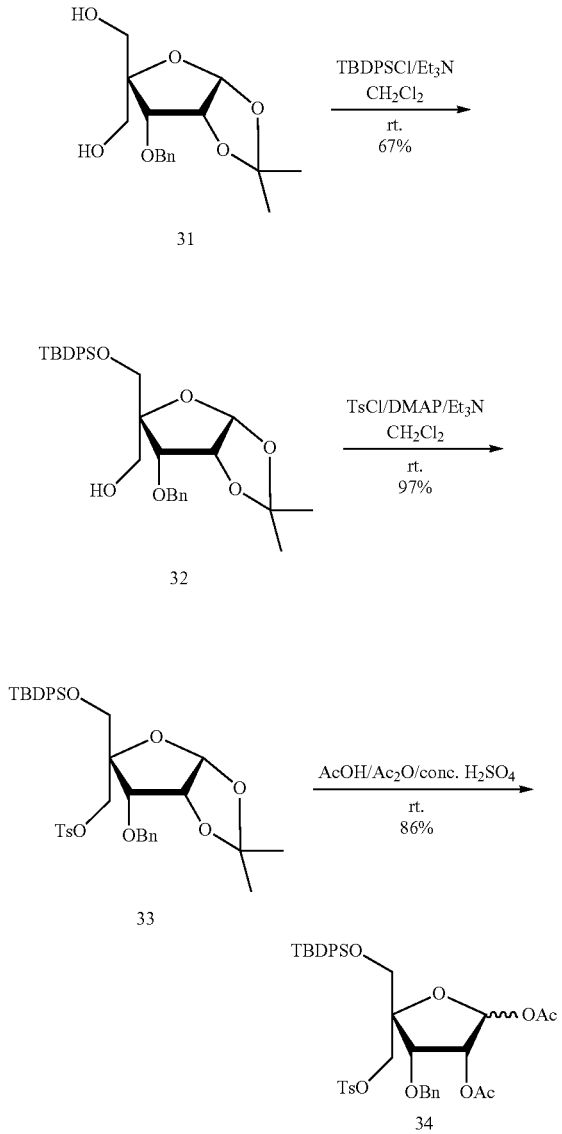

Compound 34 was condensed, separately, with thymine, benzoyladenine, and isobutyrylguanine activated upon trimethylsilylation (referred to as 2TMS.T, 2TMS.$A^{Bz}$, and 3TMS.$G^{iBu}$, respectively), to obtain Compounds 35, 40 and 44 in high yields, as indicated by the scheme offered below. Then, these condensates were subjected to deacetylation (Compounds 36, 41, 45), five-membered ring formation (Compounds 37, 42, 46), desilylation (Compounds 38, 43, 47), and further debenzylation to form desired compounds 39.

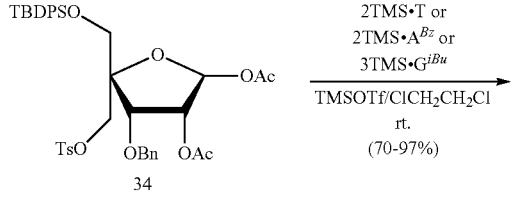

-continued

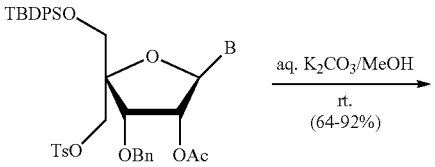

35: B = T
40: B = $A^{Bz}$
44: B = $G^{iBu}$

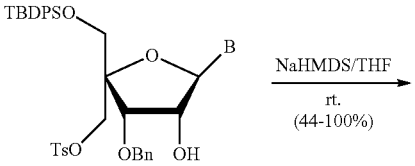

36: B = T
41: B = $A^{Bz}$
45: B = $G^{iBu}$

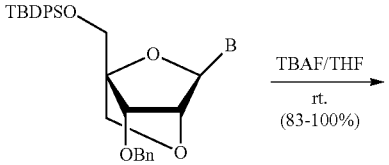

37: B = T
42: B = $A^{Bz}$
46: B = $G^{iBu}$

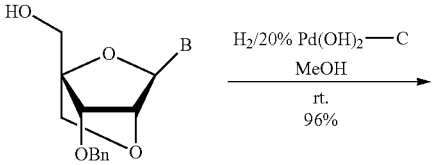

38: B = T
43: B = $A^{Bz}$
47: B = $G^{iBu}$

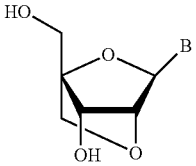

39a: B = T
39b: B = $A^{Bz}$
39c: B = $G^{iBu}$ (2) Synthesis of Oligonucleotide Analogue Compound 8 is reacted with 2-cyanoethyl-N,N,N',N'-tetraisopropylphosphoramidite to obtain an amidite compound 21. This compound is combined with a naturally occurring nucleoside amidite, and subjected to a DNA synthesizer to synthesize various oligonucleotide analogues. The synthesized crude products are purified using a reversed phase chromatographic column (Oligo-Pak). The purity of the purified product is analyzed by HPLC, whereby the formation of a purified oligonucleotide analogue can be confirmed.

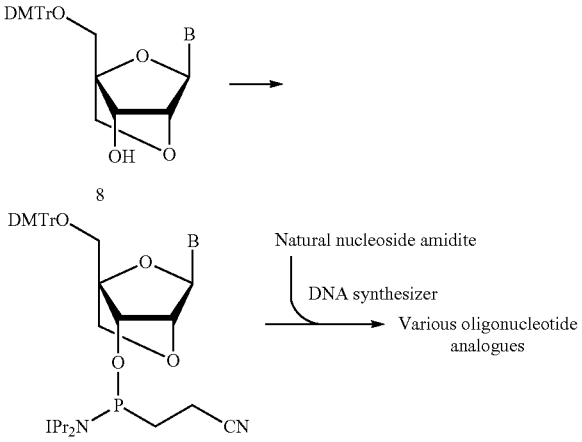

At least one monomer unit as compound 8 can be contained in the oligonucleotide analogue. Alternatively, the monomer units may be present at two or more locations in the oligonucleotide analogue in such a manner as to be separated from each other via one or more naturally occurring nucleotides. The present invention makes it possible to synthesize an antisense molecule incorporating a necessary number of the nucleotide analogues (nucleoside analogues) of the invention (a necessary length of the nucleotide or nucleoside analogue) at a necessary location. The length of the entire oligonucleotide analogue is 2 to 50, preferably 10 to 30, nucleoside units.

Such an oligonucleotide analogue (antisense molecule) is minimally degradable by various nucleases, and can be existent in vivo for a long time after administration. This antisense molecule functions, for example, to form a stable double helix together with a messenger RNA, thereby inhibiting the biosynthesis of a potentially pathogenic protein; or form a triple helix in combination with double-stranded DNA in a genome to inhibit transcription to messenger RNA. The oligonucleotide analogue can also suppress the proliferation of a virus which has infected.

In light of these findings, an oligonucleotide analogue (antisense molecule) using the nucleoside analogue of the present invention is expected to be useful as drugs, including antineoplastics and antivirals, for treatment of diseases by inhibiting the actions of particular genes.

The antisense molecule using the nucleotide (nucleoside) analogue of the present invention can be formulated into parenteral preparations or liposome preparations by incorporating customary auxiliaries such as buffers and/or stabilizers. As preparations for topical application, it may be blended with pharmaceutical carriers in common use to prepare ointments, creams, liquids or plasters.

Synthesis of the nucleoside analogue and nucleotide analogue of the present invention will be described in more detail by way of the following Examples and Production Examples. In these Examples, uracil is mainly used as a base, but other purine nucleic acid bases can also be used similarly.

EXAMPLE 1

Synthesis of Nucleoside Analogue (1) Synthesis of 2',3'-O-cyclohexylidene-4'-(p-toluenesulfonyloxymethyl)uridine (Compound 2)

To an anhydrous pyridine solution (13.5 ml) of Compound 1 (956 mg, 2.70 mmols) known in the literature, p-toluenesulfonyl chloride (771 mg, 4.05 mmols) was added at room temperature in a stream of nitrogen, and the mixture was stirred for 5 hours at 60° C.

To the reaction mixture, a saturated sodium bicarbonate solution was added, whereafter the reaction system was extracted with benzene 3 times. The organic phase was washed once with a saturated sodium chloride solution, and dried over anhydrous $MgSO_4$. The solvents were distilled off under reduced pressure, and the residue was subjected to azeotropy with benzene 3 times. The resulting crude product was purified by silica gel column chromatography ($CHCl_3$: MeOH=15:1), and then reprecipitated from benzene-hexane to obtain a white powder (Compound 2) (808 mg, 1.59 mmols, 59%).

Compound 2: White powder, m.p. 104-106° C. (benzene-hexane). IR ν (KBr): 3326, 2929, 2850, 1628, 1577, 1544, 1437, 1311, 1244 $cm^{-}$. $^1$H-NMR ($d_6$-acetone): δ 1.45-1.67 (10H, m), 2.45 (3H, s), 3.71 (2H, ABq, J=12 Hz), 4.20 (2H, ABq, J=11 Hz), 4.92 (1H, d, J'=6 Hz), 5.05, 5.06 (1H, dd, J=4.6 Hz), 5.60 (1H, d, J=7 Hz), 5.75 (1H, d, J=4 Hz), 7.48 (2H, d, J=8 Hz), 7.77 (1H, d, J=8 Hz), 7.81 (2H, d, J=8 Hz), 10.10 (1H, s,). $^{13}$C-NMR ($d_6$-acetone): δ 21.5, 24.1, 24.5, 25.5, 34.8, 36.9, 63.5, 69.7, 82.5, 84.7, 87.8, 92.9, 102.9, 115.4, 128.8, 130.8, 133.9, 142.7, 145.9, 151.3, 163.5. Mass (EI): m/z 481 ($M^+$—$H_2O$).

Anal, Calcd. for $C_{23}H_{28}N_2O_9S.⅓H_2O$: C, 53.69; H, 5.61; N, 5.44; S, 6.22. Found: C, 53.99;H, 5.48;N, 5.42;S, 6.10.

(2) Synthesis of 4'-(p-toluenesulfonyloxymethyl)uridine (Compound 3)

The above compound 2 (107 mg, 0.21 mmol) was stirred in TFA-$H_2O$ (98:2, 1 ml) for 10 minutes at room temperature. The reaction mixture was distilled off under reduced pressure, and EtOH was added to the residue, followed by performing azeotropy 3 times. The resulting crude product was purified by silica gel column chromatography ($CHCl_3$: MeOH=10:1) to obtain Compound 3 (85.0 mg, 0.20 mmol, 94%).

Compound 3: White powder, m.p. 119-120° C. IR ν (KBr): 3227, 3060, 2932, 2837, 1709, 1508, 1464, 1252, 978, 835, 763, 556 $cm^{-1}$. $^1$H-NMR ($d_6$-acetone): δ 2.31 (3H, s), 2.84 (3H, s), 3.71 (2H, s), 4.13, 4.20 (2H, ABq, J=11 Hz), 4.28, 4.31 (1H, dd, J'=9.6 Hz), 4.36 (1H, d, J'=6 Hz), 5.54 (1H, d, J'=8 Hz), 5.75 (1H, d, J=7 Hz), 7.32 (2H, d, J=8 Hz), 7.67 (2H, d, J=8 Hz), 7.70 (1H, d, J'=8 Hz), 10.14 (1H, s). $^{13}$C-NMR ($d_6$-acetone): δ 21.5, 63.7, 70.8, 72.7, 74.6, 86.8, 88.8, 103.1, 128.8, 130.7, 133.9, 141.7, 145.8, 151.8, 163.9. Mass (EI): m/z 256 ($M^+$—OTs).

(3) Synthesis of 2',3'-O-benzylidene-4'-(p-toluenesulfonyloxymethyl)uridine (Compound 4)

In a stream of nitrogen, benzaldehyde (2.4 ml, excess) and zinc chloride (670 mg, 5.0 mmols) were added to the above compound 3 (400 mg, 0.93 mmols), and the mixture was stirred for 5 hours at room temperature. After the reaction was stopped by addition of a saturated sodium bicarbonate solution, the reaction mixture was extracted with chloroform, and washed with a saturated sodium bicarbonate solution, water, and a saturated sodium chloride solution. The organic phase was dried over anhydrous sodium sulfate. The solvents were distilled off under reduced pressure, and the residue was purified by silica gel column chromatography ($CHCl_3$: MeOH=40:1) to obtain Compound 4 (380 mg, 0.74 mmol, 80%).

Compound 4: White powder. m.p. 99-102° C. ($CH_2Cl_2$-hexane). $[\alpha]_D^{23}$ −26.7° (c=1.0. $CHCl_3$). IR ν (KBr): 3059, 1691, 1460, 1362, 1269, 1218, 1177 $cm^{-1}$. $^1$H-NMR ($CDCl_3$): δ 2.41 (3H, s), 3.25 (1H, br), 3.79 (2H, m), 4.19 (2H, s), 5.09 (1H, d, J=7 Hz), 5.28 (1H, dd, J=3.7 Hz), 5.60 (1H, d, J=4 Hz), 5.73 (1H, d, J=8 Hz), 5.94 (1H, s), 7.24 (1H, d, J=8 Hz), 7.38 (2H, d, J=9 Hz), 7.42 (5H, br), 7.69 (2H, d, J=9 Hz), 9.11 (1H, br). $^{13}$C-NMR ($CDCl_3$): δ 21.6, 63.5, 68.3, 77.2, 82.8, 84.2, 87.7, 94.9, 102.6, 107.5, 126.5, 127.9, 128.5, 129.7, 132.2, 135.0, 143.0, 145.0, 150.4, 163.5.

Anal. Calcd. for $C_{24}H_{24}N_2O_9S.⅓H_2O$: C, 55.17; H, 4.76; N, 5.36; S, 6.14. Found: C, 55.19;H, 4.66;N, 5.29;S, 5.98.

(4) Synthesis of 3'-O-benzyl-4'-(p-toluenesulfonyloxymethyl)uridine (Compound 5)

To an acetonitrile solution (3 ml) of Compound 4 (150 mg, 0.29 mmol), sodium borocyanohydride (92 mg, 1.5 mmols) was added at room temperature in a stream of nitrogen. Then, titanium tetrachloride (0.16 ml, 1.5 mmols) was added dropwise under cooling with ice, and the mixture was stirred for 15 hours at room temperature. The reaction mixture was diluted with chloroform, and washed with a saturated sodium bicarbonate solution, water, and a saturated sodium chloride solution. Then, the organic phase was dried over anhydrous sodium sulfate. After the solvents were distilled off, the residue was purified by silica gel column chromatography ($CHCl_3$:MeOH=25:1) to obtain Compound 5 (112 mg, 0.22 mmol, 75%).

Compound 5: Colorless crystals. m.p. 195-197° C. (AcOEt-hexane). $[\alpha]_D^{23}$ −14.6° (c=1.0, $CHCl_3$). IR ν (KBr): 3033, 2885, 2820, 1726, 1470, 1361, 1274, 1175, 1119 $cm^{-1}$.

$^1$H-NMR ($CDCl_3$) δ: 2.40 (3H, s), 3.59-3.77 (3H, m), 4.10, 4.24 (2H, AB, J=11 Hz), 4.32 (1H, d, J=6 Hz), 4.56 (2H, m), 4.69 (1H, d, J=11 Hz), 5.52 (1H, d, J=6 Hz), 5.67 (1H, d, J=8 Hz), 7.24-7.29 (7H, m), 7.48 (1H, d, J=8 Hz), 7.70 (2H, d, J=9 Hz), 9.91 (1H, s). $^{13}$C-NMR ($CDCl_3$): δ 21.6, 63.2, 69.2, 73.6, 74.6, 78.1, 86.6, 92.9, 102.5, 127.9, 128.2, 128.3, 128.6, 129.9, 132.3, 136.9, 142.4, 145.2, 150.7, 163.8.

Anal. Calcd. for $C_{24}H_{26}N_2O_9S$: C, 55.59; H, 5.05; N, 5.40; S, 6.18. Found: C, 55.41;H, 5.02;N, 5.32; S, 6.15.

(5) Synthesis of 3'-O-benzyl-2'-O, 4'-C-methyleneuridine (Compound 6)

To an anhydrous THF solution (1.5 ml) of Compound 5 (80 mg, 0.16 mmol), an anhydrous benzene suspension (0.7 ml) of NaHMDS (3.2 mmols) was added at room temperature in a stream of nitrogen, and the mixture was stirred for 20 hours at room temperature. A saturated sodium bicarbonate solution was added to the reaction mixture, followed by extracting the mixture with $CHCl_3$. The organic phase was washed with a saturated sodium chloride solution, and then dried over anhydrous sodium sulfate. After the solvents were distilled off under reduced pressure, the resulting crude product was purified by silica gel column chromatography ($CHCl_3$: MeOH=10:1), and then recrystallized from MeOH to obtain Compound 6 (41 mg, 0.10 mmol, 61%).

Compound 6: Colorless crystals. m.p. 217-219° C. (MeOH). $[\alpha]_D^{23}$+108.4° (c=0.3, MeOH). IR ν (KBr): 3059, 2951, 1688, 1459, 1271, 1053 $cm^{-1}$. $^1$H-NMR ($d_6$-DMSO) δ: 3.75, 3.85 (2H, AB, J=8 Hz), 3.77 (2H, d, J=5 Hz), 3.92 (1H, s), 4.44 (1H, s), 4.60 (2H, s), 5.39 (1H, t, J=5 Hz), 5.48 (1H, s), 7.31 (5H, m), 7.72 (1H, d, J=8 Hz), 11.37 (1H, s).

$^{13}$C-NMR ($d_6$-DMSO) δ: 56.0, 71.1, 71.6, 75.8, 76.5, 86.5, 88.3, 100.9, 127.4, 127.6, 128.2, 137.9, 139.0, 150.0, 163.3.

Mass (EI): m/z 346 ($M^+$, 1.1).

Anal. Calcd. for $C_{17}H_{18}N_2O_6$: C, 58.96; H, 5.24; N, 8.09. Found: C, 58.67; H, 5.23; N, 8.05.

(6) Synthesis of 2'-O,4'-C-methyleneuridine (Compound 7)

To a methanol solution (2.5 ml) of Compound 6 (25 mg, 0.072 mmol), 10% Pd-C (25 mg) was added, and the mixture was stirred for 15 hours at atmospheric pressure in a stream of hydrogen. The reaction mixture was filtered, and the solvent was distilled off. Then, the residue was purified by silica gel column chromatography ($CHCl_3$:MeOH=10:1, then 5:1) to obtain Compound 7 (18.3 mg, quant.).

Compound 7: Colorless crystals. m.p. 239-243° C. (MeOH). $[\alpha]_D^{23}$+92.2° (c=0.3, MeOH). IR ν (KBr): 3331, 3091, 3059, 2961, 1689, 1463, 1272, 1049 $cm^{-1}$. $^1$H-NMR ($CD_3OD$) δ: 3.76, 3.96 (2H, AB, J=8 Hz), 3.90 (2H, s), 4.04 (1H, s), 4.28 (1H, s), 5.55 (1H, s), 5.69 (1H, d, J=8 Hz), 7.88 (1H, d, J=8 Hz).

Anal. Calcd. for $C_{10}H_{12}N_2O_6$: C, 46.88; H, 4.72; N, 10.93. Found: C, 46.74; H, 4.70; N, 10.84.

(7) 5'-O-(4,4'-dimethoxytrityl)-2'-O,4'-C-methyleneuridine (Compound 8)

To Compound 7 (140 mg, 0.53 mmol), anhydrous pyridine was added, followed by performing azeotropy of the mixture 3 times. Then, the product was converted into an anhydrous pyridine solution (1.5 ml), and 4,4'-dimethoxytrityl chloride (210 mg, 0.63 mmol) and DMAP (6.5 mg, 0.053 mmol) were added at room temperature in a stream of nitrogen. The mixture was stirred for 5 hours at room temperature. To the reaction mixture, a saturated sodium bicarbonate solution was added, followed by extraction with $CH_2Cl_2$. The organic phase was washed with water and a saturated sodium chloride solution, and then dried over anhydrous sodium sulfate. After the solvents were distilled off under reduced pressure, the resulting crude product was purified by silica gel column chromatography ($CHCl_3$:MeOH=40:1) to obtain Compound 8 (230 mg, 0.34 mmol, 66%).

Compound 8: White powder. m.p. 117-120° C. ($CHCl_3$). $[\alpha]_D^{23}$+17.2° (c=1.0, $CHCl_3$). IR ν (KBr): 3393, 3101, 2885, 1689, 1464, 1272, 1047 $cm^{-1}$. $^1$H-NMR ($CDCl_3$) δ: 2.59 (1H, br), 3.56 (2H, q, J=7, 11 Hz), 3.87 (1H, d, J=7 Hz), 4.26 (1H, s), 4.47 (1H, 5), 5.60 (1H, d, J=9 Hz), 5.63 (1H, s), 5.84 (4H, d, J=9 Hz), 7.22-7.45 (9H, m), 7.93 (1H, d, J=9 Hz).

EXAMPLE 2

Synthesis of Nucleoside Analogue (1) Synthesis of Methyl=5-O-(t-butyldiphenylsilyl)-4-hydroxymethyl-2,3-O-isopropylidene-β-D-ribofuranoside (Compound 14)

In a stream of nitrogen, $Et_3N$ (2.62 ml, 18.8 mmols) and t-butyldiphenylsilyl chloride (4.88 ml, 18.8 mmols) were added to an anhydrous $CH_2Cl_2$ solution (40 ml) of Compound 13 (2.00 g, 8.54 mmols) known in the literature under cooling with ice, and the mixture was stirred for 13 hours at room temperature. To the reaction mixture, a saturated sodium bicarbonate solution was added, whereafter the reaction system was extracted with AcOEt 3 times. The organic phase was washed once with a saturated sodium chloride solution, and then dried over anhydrous $Na_2SO_4$. The solvents were distilled off under reduced pressure, and the resulting crude product was purified by silica gel column chromatography (hexane:AcOEt=5:1) to obtain colorless oily matter (Compound 14) (2.82 g, 5.98 mmols, 70%).

$[\alpha]_D^{17}$−16.2° (c=0.52, $CHCl_3$). IR ν (KBr): 3510, 3061, 2938, 2852, 1465, 1103 $cm^{-1}$.

$^1$H-NMR ($CDCl_3$) δ: 1.09 (9H, s), 1.28 (3H, s), 1.49 (3H, s), 3.22 (3H, s), 3.67, 3.76 (2H, AB, J=11 Hz), 3.88, 3.93 (2H, AB, J=11 Hz), 4.49 (1H, d, J=6 Hz), 4.57 (1H, d, J=6 Hz), 4.93 (1H, s), 7.38-7.43 (6H, m), 7.67 (4H, d, J=7 Hz).

$^{13}$C-NMR ($CDCl_3$) $\delta_c$: 19.2, 24.4, 25.9, 26.9, 55.0, 62.9, 64.8, 82.2, 85.9, 88.7, 108.6, 112.6, 127.8, 129.9, 133.0, 135.7.

Anal. Calcd. for $C_{26}H_{36}O_6Si.¼H_2O$: C, 65.45; H, 7.71. Found: C, 65.43; H, 7.59.

(2) Synthesis of Methyl=5-O-(t-butyldiphenylsilyl)-2,3-O-isopropylidene-4-(p-toluenesulfonyloxymethyl)-β-ribofuranoside (Compound 15)

In a stream of nitrogen, $Et_3N$ (3.92 g, 28.0 mmols), p-toluenesulfonyl chloride (1.34 g, 7.22 mmols), and 4-dimethylaminopyridine (90 mg, 0.72 mmol) were added to an anhydrous $CH_2Cl_2$ solution (15 ml) of Compound 14 (2.13 g, 4.51 mmols), and the mixture was stirred for 17 hours at room temperature. To the reaction mixture, a saturated sodium bicarbonate solution was added, whereafter the reaction system was extracted with AcOEt 3 times. The organic phase was washed once with a saturated sodium chloride solution, and then dried over anhydrous $Na_2SO_4$. The solvents were distilled off under reduced pressure, and the resulting crude product was purified by silica gel column chromatography (hexane:AcOEt=10:1) to obtain colorless oily matter, Compound 15 (2.76 g, 4.42 mmols, 98%). $[\alpha]_D^{17}$−3.82° (c=0.56, $CHCl_3$). IR ν (KBr): 2934, 2852, 1369, 1104 $cm^{-1}$.

$^1$H-NMR ($CDCl_3$) δ: 1.02 (9H, s), 1.20 (3H, s), 1.32 (3H, s), 2.41 (3H, s), 3.09 (3H, s), 3.51, 3.77 (2H, AB, J=10 Hz), 4.34 (1H, d, J=6 Hz), 4.25, 4.39 (2H, AB, J=9 Hz), 4.47 (1H, d, J=6 Hz), 4.77 (1H, s), 7.28, 7.81 (4H, AB, J=9 Hz), 7.39-7.44 (6H, m), 7.62-7.65 (4H, m), 7.81 (2H, d, J=9 Hz).

$^{13}$C-NMR ($CDCl_3$) $\delta_c$: 19.2, 21.6, 24.5, 25.8, 26.8, 54.9, 62.7, 68.8, 81.9, 85.6, 87.5, 108.7, 112.8, 127.7, 127.8, 128.2, 129.6, 129.9, 132.9, 135.6, 144.4.

Anal. Calcd. for $C_{33}H_{42}O_8SSi$: C, 63.23; H, 6.75; S, 5.11. Found: C, 62.99; H, 6.53; S, 5.13.

(3) Synthesis of methyl=5-O-(t-butyldiphenylsilyl)-4-(p-toluenesulfonyloxymethyl)-β-D-ribofuranoside (Compound 16)

Trifluoroacetic acid (14 ml) was added to a THF-$H_2O$ [11 ml, 8:3 (v/v)] solution of Compound 15 (645 mg, 1.03 mmol s) at room temperature, and the mixture was stirred for 20 minutes at room temperature. The solvents were distilled off under reduced pressure, and the resulting crude product was purified by silica gel column chromatography (hexane:AcOEt=5:1) to obtain colorless oily matter, Compound 16 (464 mg, 0.79 mmol, 77%). $[\alpha]_D^{17}$ −35.8° (c=1.90,$CHCl_3$) IR ν (KBr): 3499, 3051, 2931, 2840, 1594, 1468, 1362, 1109 $cm^{-1}$.

$^1$H-NMR ($CDCl_3$) δ: 1.02(9H,s), 2.42(3H,s), 3.16(3H,s), 3.54, 3.70(2H,AB,J=10Hz), 3.97(1H,d,J=5Hz), 4.18(1H,d, J=5Hz), 4.26, 4.39(2H,AB,J=10Hz), 4.73(1H,s), 7.30(2H,d, J=8Hz), 7.36-7.44 (6H,m), 7.59-7.66(4H,m),7.78(2H,d, J=8Hz). $^{13}$C-NMR ($CDCl_3$) $\delta_c$: 19.2, 21.6. 26.7, 55.2, 66.5, 69.6, 74.0, 75.2, 76.5, 84.8, 107.5, 127.7, 128.0, 129.8, 132.6, 132.7, 132.8, 135.5, 135.6, 144.9.

Anal. Calcd for $C_{30}H_{38}SSiOS_8.¼H_2O$: C,60.94; H,6.56. Found: C, 60.94; H,6.43.

(4) Synthesis of Methyl=5-O-(t-butyldiphenylsilyl)-2-O, 4-C-methylene-β-D-ribofuranoside (Compound 17) and Methyl=5-O-(t-butyldiphenylsilyl)-3-O,4-C-methylene-β-D-ribofuranoside (Compound 18)

In a stream of nitrogen, a benzene suspension (1.6 ml) of NaHMDS (3.30 mmols) was added to an anhydrous THF solution (4 ml) of Compound 16 (194 mg, 0.33 mmol) at room temperature, and the mixture was stirred for 1 hour at room temperature. After a saturated sodium bicarbonate solution was added to the reaction mixture, the reaction solvents were distilled off, and the residue was extracted with AcOEt 3 times. The organic phase was washed once with a saturated sodium chloride solution, and then dried over anhydrous $Na_2SO_4$. The solvent was distilled off under reduced pressure, and the resulting crude product was purified by silica gel column chromatography (hexane:AcOEt=5:1) to obtain colorless oily matter, Compound 17 (48 mg, 0.116 mmol, 35%) and colorless oily matter, Compound 18 (59 mg, 0.142 mmol, 43%).

Compound 17: IR ν (KBr): 3438, 3064, 1103, 1036cm$^{-1}$.

$^{1}$H-NMR ($CDCl_3$) δ: 1.08(9H,s), 2.04(1H,br s), 3.39(3H, s), 3.65, 3.98(2H,AB,J=8Hz), 3.95,4.02(2H,AB,J12Hz), 4.02(1H,s), 4.30 (1H,s), 4.79(1H,s), 7.38-7.46(6H,m), 7.65-7.69(4H,m).

$^{13}$C-NMR ($CDCl_3$) $\delta_c$: 19.2, 26.7, 55.0, 60.7, 71.2, 73.1, 79.9, 85.5, 104.3, 127.8, 129.9, 130.0, 132.9, 135.6, 135.7.

Anal.Calcd for $C_{23}H_{30}O_5Si.¼H_2O$: C,65.68; H,7.34.Found: C,65.98; H,7.23.

Compound 18: IR ν (KBr):3456, 3058, 2938, 2852, 1467, 1108 cm$^{-1}$.

$^{1}$H-NMR ($CDCl_3$)δ: 1.10(9H,s), 3.26(3H,s), 3.71(2H,s), 4.02(1H, d,J=6Hz), 4.35,4.95(2H,d,J=7Hz), 5.01(1H,s), 5.11 (1H,d,J=6H z), 7.38-7.44(6H,m), 7.66(4H,d,J=7Hz).

$^{13}$C-NMR($CDCl_3$)$\delta_c$: 19.3, 26.8, 55.4, 63.7, 75.1, 77.9, 84.5, 86.3, 111.9, 127.8, 128.0, 129.9, 132.9, 133.0, 135.6, 135.8, 135.9.

Anal.Calcd for $C_{23}H_{30}O_5Si.¼H_2O$: C,65.91; H,7.34. Found: C, 66.07; H,7.14.

(5) Synthesis of Methyl=3-O-acetyl-5-O-(t-butyldiphenylsilyl)-2-O,4-C-methylene-β-D-ribofuranoside (Compound 19)

In a stream of nitrogen, acetic anhydride (0.38 ml, 4.08 mmols) and 4-dimethylaminopyridine (21 mg, 0.170 mmols) were added to an anhydrous pyridine solution (10 ml) of Compound 17 (704 mg, 1.70 mmols) at room temperature, and the mixture was stirred for 3 hours at room temperature. After a saturated sodium bicarbonate solution was added to the reaction mixture, the system was extracted with AcOEt 3 times. The organic phase was washed once with a saturated sodium chloride solution, and then dried over anhydrous $Na_2SO_4$. The solvents were distilled off under reduced pressure, and the resulting crude product was purified by silica gel column chromatography (hexane:AcOEt=7:1) to obtain colorless oily matter, Compound 19 (665 mg, 1.46 mmols, 86%).

$[\alpha]_D^{17}$−34.3° (c=0.93,$CHCl_3$) IR ν (KBr): 3438, 3064, 2934, 1749, 1468, 1103, 1036 cm$^{-1}$.

$^{1}$H-NMR ($CDCl_3$)δ: 0.99(9H,s), 1.97(3H,s), 3.34(3H,s), 3.69, 3.86(2H,AB,J=8Hz), 3.86(2H,s), 4.17(1H,s), 4.77(1H, s), 5.06 (1H,s), 7.28-7.39(6H,m), 7.58-7.63(4H,m).

$^{13}$C-NMR($CDCl_3$)$\delta_c$: 19.3, 20.9, 26.7, 55.0, 60.3, 72.0, 73.6, 78.3, 85.3, 104.4, 127.7, 129.8, 133.0, 135.6, 169.8.

Anal.Calcd for $C_{25}H_{32}O_6Si.¼H_2O$: C,65.12; H,7.10. Found: C, 65.27; H,7.00.

(6) Synthesis of 5'-O-(t-butyldiphenylsilyl)-2'-O,4'-C-methylene-5-methyluridine (Compound 20)

In a stream of nitrogen, O,O'-bistrimethylsilylthymine (154 mg, 0.598 mmols) was added to an anhydrous $CH_3CN$ solution (2 ml) of Compound 19 (109.2 g, 0.239 mmol) at room temperature. Then, a 1,1-dichloroethane (0.31 ml) solution of trimethylsilyltrifluoromethane sulfonate (0.82 ml, 8.74 mmols) was added under cooling with ice, and the mixture was stirred for 18 hours at room temperature. The reaction mixture was diluted with $CH_2Cl_2$, and a saturated sodium bicarbonate solution was added, followed by extracting the system with AcOEt 3 times. The organic phase was washed once with a saturated sodium chloride solution, and then dried over anhydrous $Na_2SO_4$. The solvents were distilled off under reduced pressure, and the resulting crude product was purified by silica gel column chromatography (hexane:AcOEt=3:1) to obtain colorless oily matter, Compound 20 (87.7 mg, 0.173 mmol, 70%).

IR ν (KBr): 3048, 2935, 2852, 1749, 1466, 1369, 1234, 1108, 1040 cm$^{-1}$.

$^{1}$H-NMR ($CDCl_3$)δ: 1.06(9H,s), 1.94(3H,s), 2.98(1H,br s), 3.63, 4.00(2H,AB,J=10Hz), 3.72(1H,d,J=7Hz), 3.82-3.84 (2H,m), 4.30 (1H,s), 5.25(1H,s), 7.40-7.46(6H, m), 7.60(4H, d,J=6Hz), 7.66 (1H,s), 9.68(1H,br s).

EXAMPLE 3

Synthesis of Nucleoside Analogue (Different Method)

(1) Synthesis of 3-O-benzyl-5-O-t-butyldiphenylsilyl-4-(hydroxymethyl)-1,2-O-isopropylidene-α-D -erythropentofuranose (Compound 32)

In a stream of nitrogen, triethylamine (3.71 ml, 26.6 mmols) and t-butyldiphenylsilyl chloride (6.94 ml, 26.7 mmols) were added, under cooling with ice, to a methylene chloride solution (50 ml) of Compound 31 (2.50 g, 8.08 mmols) prepared in accordance with the aforementioned reference 5). The mixture was stirred for 10.5 hours at room temperature. After a saturated sodium bicarbonate solution was added to the reaction mixture, the system was extracted with ethyl acetate. The organic phase was washed with a saturated sodium chloride solution, and then dried over sodium sulfate. The solvents were distilled off under reduced pressure, and the resulting crude product was purified by silica gel column chromatography (AcOEt-hexane:=1:4→4:3) to obtain a white solid, Compound 32 (2.97 g, 5.41 mmols, 67%).

m.p. 98-99° C. (hexane). $[\alpha]_D^{20}$+54.8° (c=1.12, acetone).

IR ν max (KBr): 3553, 2936, 1463, 1379, 1107 cm$^{-1}$.

$^{1}$H-NMR($CDCl_3$)δ: 1.13 (9H, s), 1.50 (3H, s), 1.78 (3H, s), 2.56 (1H, t, J=7 Hz), 3.82, 3.92 (2H, AB, J=11 Hz), 3.94 (2H, t, J=6 Hz), 4.57 (1H, d, J=5 Hz), 4.64, 4.95 (2H, AB, J=12 Hz), 4.83 (1H, dd, J=4, 5 Hz), 5.95 (1H, d, J=4 Hz), 7.44-7.55 (11H, m), 7.72-7.78 (4H, m). $^{13}$C-NMR($CDCl_3$) δ: 19.2, 26.2, 26.5, 26.8, 63.2, 65.4, 72.5, 77.9, 79.1, 87.4, 104.4, 113.7, 127.6, 127.7, 128.0, 128.5, 129.5, 129.7, 132.9, 133.1, 134.7, 135.5, 137.2.

Anal. Calcd for $C_{32}H_{40}O_6Si$: C, 70.04; H, 7.38. Found: C, 70.19; H, 7.35.

(2) Synthesis of 3-O-benzyl-5-O-(t-butyldiphenylsilyl)-4-(p-toluenesulfonyloxymethyl)-1,2-α-D-erythropentofuranose (Compound 33)

In a stream of nitrogen, triethylamine (395 μl, 2.83 mmols), p-toluenesulfonyl chloride (139.2 mg, 0.730 mmol), and 4-dimethylaminopyridine (8.92 mg, 0.0730 mmols) were added, under cooling with ice, to a methylene chloride solution of Compound 32 (250 mg, 0.456 mmol). The mixture was stirred for 15.5 hours at room temperature. After a saturated sodium bicarbonate solution was added to the reaction mixture, the system was extracted with ethyl acetate. The organic phase was washed with a saturated sodium chloride solution, and then dried over sodium sulfate. The solvents were distilled off under reduced pressure, and the resulting crude product was purified by silica gel column chromatography (AcOEt-hexane:=1:6) to obtain light yellow oily matter, Compound 33 (310.6 mg, 0.442 mmol, 97%).

$[\alpha]_D^{20}$+16.0° (c=0.44, acetone). IR ν max (KBr): 2935, 1595, 1462, 1363, 1174, 1106 cm$^{-1}$.

$^{1}$H-NMR ($CDCl_3$) δ: 1.08 (9H, s), 1.40 (3H, s), 1.46 (3H, s) 2.48 (3H, s) 3.68, 3.83 (2H, AB, J=11 Hz), 4,45 (2H, dd, J=4, 5 Hz), 4.64, 4.81 (2H, AB, J=12 Hz), 4.68 (1H, dd, J=4, 5 Hz), 5.81 (1H, d, J=4 Hz), 7.32 (2H, d, J=8 Hz), 7.42-7.72 (15H, m), 7.82, (2H, d, J=8 Hz), 7.66 (4H, m), 7.72 (2H, d, J=8 Hz).

$^{13}$C-NMR($CDCl_3$)$\delta_c$: 19.1, 21.5, 26.1, 26.4, 26.7, 64.4, 70.0, 72.5, 78.1, 78.9, 85.4, 104.2, 113.6, 127.3, 127.7, 127.9, 128.0, 128.4, 129.6, 129.7, 129.8, 132.7, 132.8, 135.5, 137.2, 144.4. MS(EI) m/z : 646 ($M^+$-t-Bu). High-MS (EI): Calcd for $C_{35}H_{37}O_8SSi$ ($M^+$-t-Bu): 645.1978, Found : 645.1969.

(3) Synthesis of 1,2-di-O-acetyl-3-O-benzyl-5-O-t-butyldiphenylsilyl-4-(p-toluenesulfonyloxymethyl)-α- and -η-D-ribofuranose (Compound 34)

In a stream of nitrogen, acetic anhydride (6.0 ml, 63.6 mmols) and concentrated sulfuric acid (56 μl, 1.10 μmol) were added to an acetic acid solution (56 ml) of Compound 34 (3.70 g, 5.27 mmols). The mixture was stirred for 2 hours at room temperature. The reaction mixture was emptied into iced water (300 ml), and stirred for 30 minutes. After a saturated sodium chloride solution was added, the mixture was extracted with ethyl acetate. Then, the organic phase was dried over magnesium sulfate. The solvents were distilled off, and the resulting crude product was purified by silica gel column chromatography (AcOEt-hexane, 2:1) to obtain yellow oily matter, Compound 34 (3.36 g, 4.53 mmols, 86%), as an α-β (1:4) mixture.

IR ν max (KBr): 2934, 2863, 1751, 1365, 1217 1106 $cm^{-1}$.

$^1$H-NMR ($CDCl_3$) [β-configuration] δ:1.02 (9H, s), 1.77 (3H, s), 1.98 (3H, s), 2.39 (3H, s), 3.61, 3.76 (2H, AB, J=11 Hz), 4.21-4.58 (5H, m), 5.26 (1H, d, J=5 Hz), 5.94 (1H, s), 7.15-7.59 (13H, m), 7.58-7.66 (4H, m), 7.72 (2H, d, J=8 Hz). [α-configuration] d: 1.02 (9H, s), 1.98 (3H, s), 2.36 (3H, s), 3.48, 3.58 (2H, AB, J=11 Hz), 4.21-4.58 (5H, m), 5.12 (1H, dd, J=5, 6 Hz), 6.33 (1H, d, J=5 Hz), 7.15-7.59 (13H, m), 7.58-7.66 (4H, m), 7.72 (2H, d, J=8 Hz).

$^{13}$C-NMR ($CDCl_3$) $\delta_c$: 14.2, 19.3, 20.5, 20.8, 21.6, 26.7, 26.8, 60.3, 64.8, 69.1, 73.6, 74.1, 78.6, 85.3, 97.4, 127.4, 127.6, 127.7, 127.8, 127.9, 128.0, 128.2, 128.3, 128.4, 129.5, 129.6, 1289.8, 129.9, 132.4, 132.8, 132.9, 135.4, 135.5, 135.6, 136.9, 144.5, 168.7, 169.4. High-MS(FAB): Calcd for $C_{40}H_{46}N_2O_{10}SSiNa$ ($M^+$+Na): 769.2479, Found: 769.2484.

(4) Synthesis of 2'-O-acetyl-3'-O-benzyl-5'-O-t-butyldiphenylsilyl-4'-p-toluenesulfonyloxymethyl-5-methyluridine (Compound 35)

In a stream of nitrogen, 2TMS.T (1.04 g, 4.03 mmols) and trimethylsilyltrifluoromethane sulfonate (730 μl, 4.03 mmols) were added, under cooling with ice, to a 1,2-dichloroethane solution (26 ml) of Compound 34 (1.88 g, 2.52 mmols), and the mixture was stirred for 17 hours at room temperature. A saturated sodium bicarbonate solution was added to the reaction mixture, and the system was filtered through Celite, followed by extracting the mother liquor with chloroform. The organic phase was washed with a saturated sodium chloride solution, and then dried over sodium sulfate. The solvents were distilled off under reduced pressure, and the resulting crude product was purified by silica gel column chromatography (AcOEt-hexane, 2:3) to obtain a white powder, Compound 35 (2.00 g, 2.44 mmols, 97%).

m.p. 70-71.5° C. $[\alpha]_D^{24}$+4.58° (c=1.25, acetone).

IR ν max (KBr): 3059, 2934, 1694, 1465, 1368, 704 $cm^{-1}$.

$^1$H-NMR($CDCl_3$)δ: 1.18 (9H, s), 1.63 (3H, d, J=1 Hz), 2.10 (3H, s), 2.42 (3H, s), 3.73, 3.86 (2H, AB, J=11 Hz), 4.12, 4.20 (2H, AB, J=11 Hz), 4.44, 4.57 (2H, AB, J=11 Hz), 4.45 (1H, d, J=6 Hz), 5.38 (1H, t, J=6 Hz), 6.02 (1H, d, J=6 Hz), 7.21-7.60 (13H, m), 7.62-7.69 (7H, m), 8.91 (1H, br s).

$^{13}$C-NMR($CDCl_3$)δ: 11.9, 19.3, 20.6, 21.6, 27.0, 65.3, 68.6, 74.1, 74.8, 77.2, 77.3, 86.0, 86.4, 111.6, 127.9, 128.0, 128.2, 128.5, 129.7, 130.1, 130.2, 131.8, 132.3, 132.5, 135.3, 135.5, 135.6, 136.8, 144.9, 150.2, 163.4, 170.2. MS (FAB) m/z: 813 ($M^+$+H).

Anal. Calcd for $C_{43}H_{48}N_2O_{10}SSi.2H_2O$: C, 60.83; H, 6.17; N, 3.30. Found: C, 60.55; H, 5.78; N, 3.22.

(5) Synthesis of 3'-O-benzyl-5'-O-t-butyldiphenylsilyl-4'-p-toluenesulfonyloxymethyl-5-methyluridine (Compound 36)

Potassium carbonate (12.75 mg, 0.0923 mmol) and water (0.5 ml) were added, under cooling with ice, to a methyl alcohol solution (4 ml) of Compound 35 (250 mg, 0.308 mmol), and the mixture was stirred for 22 hours at room temperature. Under cooling with ice, acetic acid was added to the reaction mixture to neutralize it, whereafter the solvent was distilled off under reduced pressure. After water was added to the residue, the mixture was extracted with ethyl acetate. The organic phase was washed with a saturated sodium chloride solution, and then dried over sodium sulfate. The solvent was distilled off under reduced pressure, and then the resulting crude product was purified by silica gel column chromatography (AcOEt-hexane, 3:2) to obtain a white powder, Compound 36 (216.7 mg, 0.283 mmol, 92%). mp. 74-77° C. $[\alpha]_D^{23}$ +5.15° (c=1.23, $CHCl_3$). IR ν max (KBr): 3048, 2934, 1695, 1363, 1181, 1108, 977, 819, 704 $cm^{-1}$.

$^1$H-NMR ($CDCl_3$) d: 1.05 (9H, s), 1.65 (3H, d, J=1 Hz), 2.39 (3H, s), 3.04 (1H, br d, J=9 Hz), 3.72 (2H, s), 4.17 (2H, s), 4.18 (1H, d, J=5 Hz), 4.24-4.32 (1H, m), 4.54, 4,62 (2H, AB, J=11 Hz), 5.62 (1H, d, J=6 Hz), 7.19-7.69 (20H, m), 8.46 (1H, br s).

$^{13}$C-NMR ($CDCl_3$) $\delta_c$: 12.1, 19.4, 26.9, 58.8, 72.0, 72.2, 75.8, 76.7, 87.4, 88.8, 110.4, 127.7, 12.79, 128.1, 128.2, 128.5, 128.7, 129.8, 130.0, 130.1, 132.2, 134.3, 135.3, 135.5, 136.8, 149.8, 163.9. MS(FAB) m/z: 771 ($M^+$+H).

Anal. Calcd for $C_{41}H_{46}N_2O_9SSi$: C, 63.41; H, 6.16; N, 3.51; S, 3.95. Found: C, 63.87; H, 6.01; N, 3.63; S, 4.16.

(6) Synthesis of 3'-O-benzyl-5'-O-t-butyldiphenylsilyl-2'-O,4'-C-methylene-5-methyluridine (Compound 37)

In a stream of nitrogen, sodium bis(trimethylsilyl)amide (1.0 M in THF, 8.47 ml, 8.47 mmols) was added, under cooling with ice, to a tetrahydrofuran solution (30 ml) of Compound 36 (1.86 g, 2.42 mmols), and the mixture was stirred for 1 hour at room temperature. A saturated sodium bicarbonate solution (14 ml) was added to the reaction mixture, and then the solvent was distilled off under reduced pressure. After water was added to the residue, the mixture was extracted with chloroform. The organic phase was washed with a saturated sodium chloride solution, and then dried over sodium sulfate. The solvents were distilled off under reduced pressure, and the resulting crude product was purified by silica gel column chromatography (AcOEt-hexane, 2:3) to obtain a white powder, Compound 37 (1.42 g, 2.37 mmols, 98%).

m.p. 70.5-72° C. $[\alpha]_D^{22}$+52.47° (c=1.025, acetone). IR ν max (KBr): 2936, 1694, 1465, 1275, 1106, 1055, 809, 704 $cm^{-1}$.

$^1$H-NMR($CDCl_3$)δ: 1.21 (9H, s), 1.76 (3H, s), 3.88, 4.07 (2H, AB, J=8 Hz), 4.07, 4.15 (2H, AB, J=11 Hz), 4.16 (1H, s), 4.66, 4.80 (2H, AB, J=11 Hz), 4.76 (1H, s), 7.34-7.79 (16H, m), 10.0 (1H, br s). MS (FAB) m/z: 599 ($M^+$+H).

Anal. Calcd for $C_{34}H_{38}N_2O_6Si.2H_2O$: C, 64.33; H, 6.03; N, 4.41. Found: C, 64.58; H, 6.15; N, 4.28.

(7) Synthesis of 3'-O-benzyl-2'-O,4'-C-methylene-5-methyluridine (Compound 38)

In a stream of nitrogen, tetrabutylammonium fluoride (1.0 M in THF, 379 μl, 0.379 μmol) was added to a tetrahydrofuran solution (1 ml) of Compound 37 (188.7 mg, 0.316 mmol), and the mixture was stirred for 2.5 hours at room temperature. The reaction mixture was distilled under reduced pressure, and the resulting crude product was purified by silica gel column chromatography (AcOEt-hexane, 1:1→1:0) to obtain a white powder, Compound 38 (94.6 mg, 0.262 mmol, 83%).

IR ν max (KBr): 3424, 3183, 3063, 2950, 1691, 1463, 1273, 1057, 734 $cm^{-1}$.

$^1$H-NMR ($CDCl_3$)δ: 1.90(3H, d, J=1 Hz), 3.83, 4.05(2H, AB, J=8 Hz), 3.93, 4.02(2H, AB, J 12 Hz), 3.94(1H, s), 4.53(1H, s), 4.56, 4.58(2H, AB, J=12 Hz), 5.65 (1H, s), 7.32 (5H, s), 7.44(1H, d, J=1 Hz). High-MS (EI): Calcd for $C_{18}H_{20}NO_6$ ($M^+$): 360.1321, Found 360.1312.

(8) Synthesis of 2'-O,4'-C-methylene-5-methyluridine (Compound 39a)

To a methyl alcohol solution (4 ml) of Compound 38 (86.5 mg, 0.240 mmol), 20% $Pd(OH)_2$-C (86.5 mg) was added, and the mixture was stirred for 14.5 hours at atmospheric pressure in a stream of hydrogen. The reaction mixture was filtered, and then the solvent was distilled off under reduced pressure to obtain colorless crystals, Compound 39 (62.5 mg, 0.230 mmol, 96%).

mp. 194-195° C. $[\alpha]_D^{20}$+53.7° (c=1.02, EtOH). IR ν max (KBr): 3323, 3163, 3027, 2889, 2826, 1689, 1471, 1276, 1057 $cm^{-1}$.

$^1$H-NMR ($CD_3OD$) δ: 1.89 (3H, q, J=1 Hz), 3.74, 3.95 (2H, AB, J=8 Hz), 3.90 (1H, s), 4.07 (1H, s), 4.26 (1H, s), 5.53 (1H, s), 7.74 (1H, d, J=1 Hz).

$^{13}$C-NMR ($CD_3OD$) δc: 12.6, 57.6, 70.3, 72.4, 80.8, 88.3, 90.4, 110.7. 136.8, 151.8, 166.5.

EXAMPLE 4

(1) Synthesis of 2'-O-acetyl-3'-O-benzyl-5'-O-t-butyldiphenylsilyl-4'-p-toluenesulfonyloxymethyl-$N^6$-benzoyladenosine (Compound 40)

In a stream of nitrogen, a 1,2-dichloroethane solution (5.0 ml) of Compound 34 (250 mg, 0.336 mmol) and trimethylsilyltrifluoromethane sulfonate (6.7 μl, 0.0336 mmols) were added, at room temperature, to 2TMS.$A^{Bz}$ (128.7 mg, 0.336 mmol) prepared In accordance with a reference 6) (H. Vorbrggen, K. Krolikiewicz and B. Bennua, Chem., Ber., 114, 1234-1255 (1981)). The mixture was heated under reflux for 26 hours. After a saturated sodium bicarbonate solution was added to the reaction mixture, the system was extracted 3 times with methylene chloride. The organic phase was washed with a saturated sodium chloride solution, and then dried over sodium sulfate. The solvents were distilled off under reduced pressure, and the resulting crude product was purified by silica gel column chromatography ($CHCl_3$MeOH, 1:3) to obtain a white powder, Compound 40 (234.5 mg, 0.253 mmol, 75%).

m.p. 77-78° C. (AcOEt/hexane). $[\alpha]_D^{24}$ 13.2° (c=1.00, $CHCl_3$).

IR ν max (KBr): 3058, 2934, 1749, 1703, 1606, 1105 $cm^{-1}$.

$^1$H-NMR ($CDCl_3$)δ: 0.99 (9H, s), 2.04 (3H, s), 2.38 (3H, s), 3.74, 3.85 (2H, AB, J=11 Hz), 4.31, 4.43 (2H, AB, J=11 Hz), 4.52, 4.58 (2H, AB, J=11 Hz), 4.81 (1H, d, J=6 Hz), 5.94 (1H, d, J=6 Hz), 6.04 (1H, d, J=5 Hz), 7.18-7.61 (20H, m), 7.69 (2H, d, J=8 Hz), 7.99 (1H, s), 8.01 (2H, d, J=7 Hz), 8.56 (1H, s), 8.99 (1H, br s). $^{13}$C-NMR ($CDCl_3$) δc: 19.1, 20.5, 21.5, 26.7, 64.1, 68.4, 74.0, 74.6, 77.9, 86.57, 86.64, 123.4, 127.7, 127.8, 127.9, 128.1, 128.5, 128.8, 129.6, 129.9, 132.0, 132.3, 132.6, 132.7, 133.5, 135.4, 135.5, 136.8, 142.0, 144.7, 149.6, 151.2, 152.6, 164.5, 169.8. MS(FAB) m/z: 926 ($M^+$+H).

(2) Synthesis of 3'-O-benzyl-5'-O-t-butyldiphenylsilyl-4'-p-toluenesulfonyloxymethyl-$N^6$-benzoyladenosine (Compound 41)

To a methyl alcohol solution (3.0 ml) of Compound 40 (167.9 mg, 0.182 mmol), potassium carbonate (15.0 mg, 0.109 mmol) was added at room temperature, and the mixture was stirred for 15 minute at room temperature. Concentrated hydrochloric acid was added to the reaction mixture to neutralize it, whereafter the system was extracted 3 times with methylene chloride. The organic phase was washed with a saturated sodium chloride solution, and then dried over sodium sulfate. The solvents were distilled off under reduced pressure, and the resulting crude product was purified by silica gel column chromatography ($CHCl_3$-MeOH, 30:1) to obtain a white powder, Compound 41 (140.5 mg, 0.160 mmol, 88%).

m.p. 82-83° C. (AcOEt-hexane). $[\alpha]_D^{25}$ −6.02° (c=0.96, $CHCl_3$).

IR ν max (KBr): 3306, 3066, 2935, 2859, 1701, 1611 $cm^{-1}$.

$^1$H-NMR ($CDCl_3$) δ: 0.98 (9H, s), 2.37 (3H, s), 3.76 (2H, s), 4.39, 4.45 (1H, AB, J=11 Hz), 4.54 (1H, d, J=6 Hz), 4.67, 4.76 (2H, AB, J=11 Hz), 4.85 (1H, dd, J=5, 6 Hz), 5.79 (1H, d, J=5 Hz), 7.20-7.58 (21H, m), 7.73 (2H, d, J=8 Hz), 7.80 (1H, s), 7.96 (2H, d, J=8 Hz), 8.49 (1H, s), 9.18 (1H, br s).

$^{13}$C-NMR ($CDCl_3$) δc: 19.1, 21.6, 26.8, 64.4, 68.9, 74.1, 74.6, 79.2, 86.8, 89.8, 123.1, 127.7, 127.8, 128.0, 128.2, 128.4, 128.6, 128.8, 129.7, 130.0, 132.1, 132.5, 132.6, 132.8, 133.4, 135.4, 135.5, 136.8, 142.1, 144.8, 149.4, 152.3, 164.5.

(3) Synthesis of 3'-O-benzyl-5'-O-t-butyldiphenylsilyl-2'-O,4'-C-methylene-$N^6$-benzyladenosine (Compound 42)

In a stream of nitrogen, sodium bis(trimethylsilyl)amide (1.0 M in THF, 0.58 ml, 0.572 mmol) was added to a tetrahydrofuran solution (8.0 ml) of Compound 41 (210.5 mg, 0.238 mmol) at room temperature, and the mixture was stirred for 3 hours at room temperature. A saturated sodium bicarbonate solution was added to the reaction mixture, and then the system was extracted 3 times with methylene chloride. The organic phase was washed with a saturated sodium chloride solution, and then dried over sodium sulfate. The solvents were distilled off under reduced pressure, and the resulting crude product was purified by silica gel column chromatography ($CHCl_3$-MeOH, 30:1) to obtain a white powder, Compound 42 (169.5 mg, 0.238 mmol, quant.).

mp. 80-81° C. IR ν max (KBr): 3259, 3064, 2932, 2858, 1703, 1607 $cm^{-1}$.

$^1$H-NMR($CDCl_3$)δ: 1.07 (9H, s), 3.95, 4.10 (2H, AB, J=8 Hz), 4.02 (2H, d, J=8 Hz), 4.56, 4.64 (2H, AB, J=12 Hz), 4.26 (1H, s), 4.86 (1H, s), 6.14 (1H, s), 7.26-7.70 (18H, m), 8.04 (2 H, d, J=7 Hz), 8.22 (1H, s), 8.78 (1H, s), 9.18 (1H, brs).

$^{13}$C-NMR($CDCl_3$) δc: 19.2, 26.5, 26.8, 29.7, 59.2, 72.4, 72.6, 76.5, 76.8, 86.7, 88.6, 123.4, 127.7, 127.8, 127.9, 128.1, 128.4, 128.8, 129.5, 130.0, 132.4, 132.5, 132.8, 133.5, 134.8, 135.2, 135.5, 135.6, 136.8, 140.4, 152.7.

(4) Synthesis of 3'-O-benzyl-2'-O,4'-C-methylene-$N^6$-benzoyladenosine (Compound 43)

Tetrabutylammonium fluoride (1.0 M in THF, 1.0 ml, 1.0 mmol) was added, at room temperature, to a tetrahydrofuran solution (7.0 ml) of Compound 42 (173.6 mg, 0.244 mmol), and the mixture was stirred for 25 minutes at room temperature. The reaction mixture was distilled under reduced pressure, and the resulting crude product was purified by silica gel column chromatography ($CHCl_3$-MeOH, 15:1) to obtain a white powder, Compound 43 (115.4 mg, 0.244 mmol, quant.).

mp. 154-155° C. (Et2O). IR ν max(KBr): 3339, 2944, 1701, 1611 $cm^{-1}$.

$^1$H-NMR($CDCl_3$)δ: 3.91, 4.13 (2H, AB, J=8 Hz), 3.93, 4.01 (2H, AB, J=12 Hz), 4.38 (1H, s), 4.64 (1H, s), 4.85 (1H, s), 6.08 (1H, s), 7.29 (1H, s), 7.51 (2H, d, J=8 Hz), 7.58 (1H, d, J=7 Hz), 8.05 (2H, d, J=7 Hz), 8.14 (1H, s), 8.75 (1H, s), 9.50 (1H, br s).

$^{13}$C-NMR($CDCl_3$)δc: 57.1, 72.4, 77.0, 77.1, 86.9, 88.6, 122.9, 127.6, 128.0, 128.1, 128.4, 128.7, 132.8, 133.5, 136.9, 140.5, 149.8, 150.5, 152.8, 165.0.

EXAMPLE 5

(1) Synthesis of 2'-O-acetyl-3'-O-benzyl-5'-O-t-butyldiphenylsilyl-4'-p-toluenesulfonyloxymethyl-$N^2$-isobutyrylguanosine (Compound 44)

In a stream of nitrogen, a 1,2-dichloroethane solution (5.0 ml) of Compound 4 (250 mg, 0.336 mmol) and trimethylsilyltrifluoromethane sulfonate (6.7 μl, 0.0336 mmol) were added, at room temperature, to 3TMS.$G^{iBu}$ (146.8 mg, 0.336 mmol) prepared in accordance with the aforementioned reference 6). The mixture was heated under reflux for 15 hours. After a saturated sodium bicarbonate solution was added to the reaction mixture, the system was extracted 3 times with methylene chloride. The organic phase was washed with a saturated sodium chloride solution, and then dried over sodium sulfate. The solvents were distilled off under reduced pressure, and the resulting crude product was purified by silica gel column chromatography ($CHCl_3$-MeOH, 30:1) to obtain a white powder, Compound 44 (213.6 mg, 0.235 mmol, 70%).

m.p. 96-97° C. (AcOEt-hexane). $[\alpha]_D^{24}$ −11.09° (c=0.97, $CHCl_3$).

IR ν max (KBr): 3152, 3065, 2934, 1746, 1681, 1606 $cm^{-1}$.

$^1$H-NMR ($CDCl_3$) d: 0.96 (9H, s), 1.10 (3H, d, J=9 Hz), 1.13 (3H, d, J=9 Hz), 1.98 (3H, s), 2.36 (3H, s), 2.48 (1H, m), 3.65, 3.72 (2H, AB, J=11 Hz), 4.23, 4.43 (2H, AB, J=11 Hz), 4.47 (2H, s), 4.63 (1H, d, J=6 Hz), 5.74 (1H, t, J=6 Hz), 5.96 (1H, d, J=6 Hz), 7.14-7.68 (20H, m), 9.15 (1H, s), 12.20 (1H, s).

$^{13}$C-NMR($CDCl_3$)δc: 19.1, 19.3, 19.4, 20.8, 21.9, 27.0, 27.2, 36.5, 64.5, 68.9, 74.4, 74.9, 76.7, 86.1, 86.7, 122.0, 127.6, 127.7, 127.9, 128.1, 128.3, 128.4, 128.8, 130.1, 130.4, 132.3, 132.7, 132.9, 135.7, 135.8, 137.3, 137.8, 145.2, 147.8, 148.5, 156.2, 170.2, 178.8.

(2) Synthesis of 3'-O-benzyl-5'-O-t-butyldiphenylsilyl-4'-p-toluenesulfonyloxymethyl-$N^2$-isobutyrylguanosine (Compound 45)

To a methyl alcohol solution (3.0 ml) of Compound 44 (137.0 mg, 0.151 mmol), potassium carbonate (15.8 mg, 0.113 mmol) was added at room temperature, and the mixture was stirred for 45 minutes at room temperature. Concentrated hydrochloric acid was added to the reaction mixture to neutralize it, whereafter the system was extracted 3 times with methylene chloride. The organic phase was washed with a saturated sodium chloride solution, and then dried over sodium sulfate. The solvents were distilled off under reduced pressure, and the resulting crude product was purified by silica gel column chromatography ($CHCl_3$-MeOH, 30:1) to obtain a white powder, Compound 45 (83.4 mg, 0.097 mmol, 64%).

mp. 102-103° C. (AcOEt-hexane). $[\alpha]_D^{25}$ −2.00° (c 0.40, $CHCl_3$). IR ν max(KBr): 3166, 2932, 1684, 1607 $cm^{-1}$.

$^1$H-NMR ($CDCl_3$) δ: 0.90 (9H, s), 1.09 (3H, d, J=7 Hz), 1.13 (3H, d, J=7 Hz), 2.30 (1H, m), 2.37 (3H, s), 3.71, 3.76 (2H, AB, J=11 Hz), 4.32, 4.48 (2H, AB, J=11 Hz), 4.35 (1H, d, J=6 Hz), 4.63, 4.90 (2H, AB, J=12 Hz), 4.96 (1H, t, J=6 H z), 5.67 (1H, d, J=7 Hz), 7.17-7.71 (20H, m), 8.82 (1H, s), 12.05 (1H, br s).

$^{13}$C-NMR(CDCl3)δc: 18.7, 19.0, 21.6, 26.5, 36.2, 63.5, 69.1, 73.7, 74.3, 78.8, 86.2, 89.5, 127.7, 127.8, 128.0, 128.1, 128.5, 129.7, 130.0, 132.0, 132.6, 132.7, 135.3, 135.4, 137.4, 138.2, 144.8, 146.9, 155.5, 178.5.

(3) Synthesis of 3'-O-benzyl-5'-O-t-butyldiphenylsilyl-2'-O,4'-C-methylene-$N^2$-isobutyrylguanosine (Compound 46)

In a stream of nitrogen, sodium bis(trimethylsilyl)amide (1.0 M in THF, 0.31 ml, 0.315 mmol) was added to a tetrahydrofuran solution (3.0 ml) of Compound 45 (92.1 mg, 0.102 mmol) at room temperature, and the mixture was stirred for 3 hours at room temperature. A saturated sodium bicarbonate solution was added to the reaction mixture, and then the system was extracted 3 times with methylene chloride. The organic phase was washed with a saturated sodium chloride solution, and then dried over sodium sulfate. The solvents were distilled off under reduced pressure, and the resulting crude product was purified by silica gel column chromatography ($CHCl_3$-MeOH, 25:1) to obtain a white powder, Compound 46 (31.4 mg, 0.160 mmol, 44%).

mp. 99-100° C. IR ν max(KBr): 3162, 3068, 2932, 1683, 1610 $cm^{-1}$.

$^1$H -NMR($CDCl_3$)δ: 1.06 (9H, s), 1.25 (3H, d, J=7 Hz), 1.27 (3H, d, J=7 Hz), 2.64 (1H, m), 3.83, 4.01 (2H, AB, J=8 Hz), 3.97 (2H, d, J=7 Hz), 4.18 (1H, s), 4.51 (1H, s), 4.54 (2H, d, J=2 Hz), 5.77 (1H, s), 7.17-7.42 (5H, m), 7.64-7.72 (10H, m), 7.84 (1H, s), 9.03 (1H, s), 12.08 (1H, br s).

$^{13}$C-NMR($CDCl_3$)δc: 18.9, 19.0, 19.1, 26.5, 26.7, 36.4, 59.1, 72.4, 72.5, 76.8, 77.5, 86.3, 88.3, 121.7, 127.6, 127.7, 127.8, 127.9, 128.1, 128.4, 129.6, 130.0, 132.36, 132.42, 134.8, 135.45, 135.54, 135.8, 136.8, 146.8, 147.7, 155.4, 178.6.

(4) Synthesis of 3'-O-benzyl-2'-O,4'-C-methylene-$N^2$-isobutyrylguanosine (Compound 47)

Tetrabutylammonium fluoride (1.0 M in THF, 0.90 ml, 0.90 mmol) was added, at room temperature, to a tetrahydrofuran solution (3.0 ml) of Compound 46 (41.3 mg, 0.060 mol), and the mixture was stirred for 1 hour at room temperature. The reaction mixture was distilled under reduced pressure, and the resulting crude product was purified by silica gel column chromatography (Ac0H-EtOH, 20:1) to obtain a white powder, Compound 47 (27.1 mg, 0.060 mmol, quant.).

mp. 228-229° C. (Et2O). $[\alpha]_D^{25}$ +32.90° (c=0.875, $CHCl_3$)

IR ν max (KBr): 3162, 2934, 1683, 1608 $cm^{-1}$.

$^1$H-NMR ($CDCl_3$) δ: 1.24 (3H, d, J=7 Hz), 1.26 (3H, d, J=7 Hz), 2.76 (1H, m), 3.83, 4.03 (2H, AB, J=8 Hz), 3.92, 4.02 (2H, AB, J=13 Hz), 4.33 (1H, s), 4.55 (1H, s), 4.62 (2H, s), 5.80 (1H, s), 7.25 (5H, s), 7.91 (1H, s), 9.85 (1H, s), 12.05 (1H, s).

$^1$C-NMR ($CDCl_3$) δc: 19.19, 19.25, 36.4, 57.4, 72.5, 77.0, 77.5, 86.5, 88.8, 121.0, 127.8, 128.1, 128.2, 128.3, 128.4, 128.6, 137.1, 137.5, 147.5, 148.2, 155.7, 179.9.

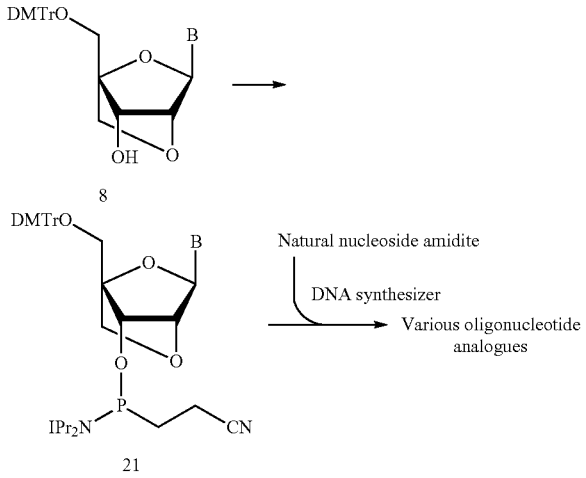

-continued

| | | |
|---|---|---|
| 5'-GCGXTTTTTGCT-3' | (XT5) | (SEQ ID NO: 2) |
| 5'-GCGTTXTTTGCT-3' | (T2XT3) | (SEQ ID NO: 3) |
| 5'-GCGTTTXTTGCT-3' | (T3XT2) | (SEQ ID NO: 4) |
| 5'-GCGTTTTTXGCT-3' | (T5X) | (SEQ ID NO: 5) |
| 5'-GCGXXTTTTGCT-3' | (X2T4) | (SEQ ID NO: 6) |
| 5'-GCGTTXXTTGCT-3' | (T2X2T2) | (SEQ ID NO: 7) |
| 5'-GCGTTTTXXGCT-3' | (T4X2) | (SEQ ID NO: 8) |
| 5'-GCGXXXXXXGCT-3' | (X6) | (SEQ ID NO: 9) |
| 5'-GTTTTTTTTXXC-3' | (X2) | (SEQ ID NO: 11) |

X =

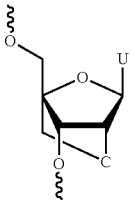

(1) 3,'-O-[2-cyanoethoxy(diisopropylamino)phosphino]-5'-O-(4,4'-dimethoxytrityl)-2'-O,4-methanouridine (Compound 21)

Compound 8 (200 mg, 0.31 mmol) and diisopropylammonium tetrazolide (39.6 mg, 0.23 mmol) were subjected to azeotropy with anhydrous $CH_3CN$ three times, and then the system was converted into an anhydrous $CH_3CN$-anhydrous THF solution (3:1, 4 ml). In a stream of nitrogen, 2-cyanoethyl N,N,N',N'-tetraisopropylphosphorodiamidite (0.12 ml, 0.37 mmol) was added, and the mixture was stirred for 90 minutes at room temperature, The solvents were distilled off under reduced pressure, and the resulting crude product was purified by silica gel column chromatography (AcOEt:hexane:$Et_3N$=75:25:1). Then, the purified product was reprecipitated from AcOEt-hexane to obtain an amidite compound 21 (181 mg, 0.25 mmol, 81%).

m.p. 71-74° C. (AcOEt-hexane).

$^{31}$P-NMR ($CDCl_3$): δ 149.6, 149.5, 149.4, 149.3, 149.2.

(2) General Synthesis of Oligonucleotide Analogues

The synthesis of an oligomer was performed by means of Pharmacia's DNA synthesizer, Gene Assembler Plus, on a 0.2 μmol scale. The concentrations of solvents, reagents, and phosphoramidite were the same as for the synthesis of natural DNA. A DMTr group of 5'-O-DMTr-thymidine (0.2 μmol) having a 3'-hydroxyl group bound to a CPG support was deprotected with trichloroacetic acid. On its 5'-hydroxyl group, condensation reaction was repeated using an amidite comprising four nucleic acid bases for natural DNA synthesis and Compound 21 to synthesize oligonucleotide analogues of respective sequences. The synthetic cycle was as follows:

| Synthetic cycle (0.2 μmol scale) | |
|---|---|
| 1) Detritylation | 1% $CCl_3COOH$ in $CH_2ClCH_2Cl$, 6 sec |
| 2) Coupling | 0.1M phosphoramidite (25 equiv.), 0.5M 1H-tetrazole (500 equiv.) in MeCN, 2 min |
| 3) Capping | 3% 4-(dimethylamino)pyridine, 10% $Ac_2O$, in MeCN, 18 sec |
| 4) Oxidation | 0.01M $I_2$ in 2,4,6-collidine/$H_2O$/MeCN (1:5:11), 6 sec |

The synthesized oligomer was cleaved from the support by treatment with concentrated aqueous ammonia in the customary manner. At the same time, the protective cyano-ethyl group was detached from the phosphorus atom, and the protective groups for the adenine, guanine and cytosine were also removed.

The resulting 5'-O-dimethoxytritylated oligonucleotide analogue was rid of the DMTr group by use of 5 ml trifluoroacetic acid on a reversed phase chromatographic column (Millipore, Oligo-Pak™SP), and further purified to obtain the desired oligonucleotide analogue.

In accordance with the foregoing method for general synthesis, the following oligonucleotide analogues were synthesized:

```
(2) 5'-GCGXTTTTTGCT-3'(XT5)      (SEQ ID NO: 2)
    Yield 0.06 μmol (30% yield)

(3) 5'-GCGTTXTTTGCT-3'(T2XT3)    (SEQ ID NO: 3)
    Yield 0.05 μmol (25% yield)

(4) 5'-GCGTTTXTTGCT-3'(T3XT2)    (SEQ ID NO: 4)
    Yield 0.03 μmol (15% yield)

(5) 5'-GCGTTTTTXGCT-3'(T5X)      (SEQ ID NO: 5)
    Yield 0.06 μmol (30% yield)

(6) 5'-GCGXXTTTTGCT-3'(X2T4)     (SEQ ID NO: 6)
    Yield 0.06 μmol (30% yield)

(7) 5'-GCGTTXXTTGCT-3'(T2X2T2)   (SEQ ID NO: 7)
    Yield 0.05 μmol (25% yield)

(8) 5'-GCGTTTTXXGCT-3'(T4X2)     (SEQ ID NO: 8)
    Yield 0.06 μmol (30% yield)

(9) 5'-GCGXXXXXXGCT-3'(X6)       (SEQ ID NO: 9)
    Yield 0.06 μmol (30% yield)

(10) 5'-GTTTTTTTTXXC-3'(X2)      (SEQ ID NO: 11)
     Yield 0.07 μmol (35% yield)
```

EXPERIMENTAL EXAMPLE 1

Measurement of Melting Temperature (Tm)

The melting temperatures (Tm's) of annealing products between antisense strands, which were the various oligonucleotide analogues synthesized in Example 2, and natural DNA- or RNA-based sense strands were measured to investigate the hybridizing ability of the oligonucleotide analogues of the present invention for complementary DNA and RNA.

Each sample solution (500 μL) with end concentrations of 100 mM NaCl, 10 mM sodium phosphate buffer (pH 7.2), 4 μM antisense strand, and 4 μM sense strand, respectively, was bathed in boiling water, and slowly cooled to room temperature over the course of 10 hours. The sample solution was gradually cooled to 5° C., kept at 5° C. for a further period of 20 minutes, and then started to be measured, with a stream of nitrogen being passed through a cell chamber of a spectrophotometer (UV-2100PC, Shimadzu) for prevention of moisture condensation. The sample temperature was raised at a rate of 0.2° C./minute until 90° C., and the ultraviolet absorption at 260 nm was measured at intervals of 0.1° C. To prevent changes in the sample concentration with increases in the temperature, the cell was provided with a closure, and a drop of a mineral oil was applied onto the surface of the sample solution during measurement.

The results are shown in the following table.

TABLE 1

Melting Temperatures (Tm's) of Antisense Oligonucleotide Analogues for Complementary DNA and RNA

| Antisense molecule | Tm for complementary DNA[a)] (ΔTm/mod.) | Tm for complementary RNA[b)] (ΔTm/mod.) |
|---|---|---|
| 5'-GCGTTTTTTGCT-3' (natural) (SEQ ID NO: 1) | 47° C. | 45° C. |

TABLE 1-continued

Melting Temperatures (Tm's) of Antisense Oligonucleotide Analogues for Complementary DNA and RNA

| Antisense molecule | Tm for complementary DNA[a)] (ΔTm/mod.) | Tm for complementary RNA[b)] (ΔTm/mod.) |
|---|---|---|
| 5'-GCGXTTTTTGCT-3' (XT5) (SEQ ID NO: 2) | 50° C. (+3° C.) | 49° C. (+4° C.) |
| 5'-GCGTTXTTTGCT-3' (T2XT3) (SEQ ID NO: 3) | 49° C. (+2° C.) | 49° C. (+4° C.) |
| 5'-GCGTTTXTTGCT-3' (T3XT2) (SEQ ID NO: 4) | 49° C. (+2° C.) | 50° C. (+5° C.) |
| 5'-GCGTTTTTXGCT-3' (T5X) (SEQ ID NO: 5) | 52° C. (+4° C.) | 51° C. (+6° C.) |
| 5'-GCGXXTTTTGCT-3' (X2T4) (SEQ ID NO:6) | 51° C. (+2° C.) | 53° C. (+4° C.) |
| 5.-GCGTTXXTTGCT-3' (T2X2T2) (SEQ ID NO: 7) | 49° C. (+1° C.) | 53° C. (+4° C.) |
| 5 -GCGTTTTXXGCT-3' (T4X2) (SEQ ID NO: 8) | 54° C. (+3.5° C.) | 55° C. (+5° C.) |
| 5'-GCGXXXXXXGCT-3' (X6) (SEQ ID NO: 9) | 58° C. (+1.8° C.) | 71° C. (+4.3° C.) |

[a)]3'-CGCAAAAAACGA-5'. (SEQ ID NO: 12)
[b)]3'-r(CGCAAAAAACGA).

As shown in the table, in the case of the oligomer having one or two units (X) of the nucleoside analogue of the present invention (general formula (Ia)) introduced into a natural DNA strand, the ability to hybridize with the complementary DNA oligomer, evaluated by the Tm, rose by 2 to 7 degrees (about 2 degrees per modified residue) as compared with the natural strand. With the oligomer having all T's substituted by X's (X6), the increase in the ability was as high as 11 degrees. When the ability to hybridize with complementary RNA was evaluated, the oligomer incorporating one or two X's had an increase in Tm of 4-10 degrees (4 to 6 degrees per modified residue) over the natural strand. In the case of X6, the ability to hybridize with complementary RNA was further enhanced, showing an increase in Tm of more than 25 degrees (4 degrees per modified residue). There have been no examples of analogues undergoing such increases in Tm as compared with natural strands, and the affinity of the claimed oligomer was higher for RNA than for DNA. These facts mean that the oligonucleotide analogue composed of the bicyclooligonucleoside analogue of the present invention has extremely high performance as an antisense molecule, and is useful as a material for pharmaceuticals.

EXPERIMENTAL EXAMPLE 2

Measurement of Nuclease Resistance

A buffer solution (0.003 U/ml, 400 μl) of a snake venom phosphodiesterase was mixed with a buffer solution (10 μM, 400 μl) of the oligonucleotide held at 37° C. for 15 minutes. The mixed solution was placed in a quartz cell (800 μl) kept at 37° C., and increases in the ultraviolet absorption (260 nm) due to the decomposition of the oligonucleotide were measured over time by means of SHIMADZU UV-2100PC. The buffer used comprised 0.1 M Tris-HCl (pH 8.6), 0.1 M NaCl, and 14 mM $MgCl_2$, and was sufficiently degassed before measurement.

Measurement of Half-life ($t_{1/2}$)

A calculation was made of the average of the values of the UV absorption measured at the start of measurement (t=0) and that measured at the time when no increase in this parameter was noted. The time corresponding to this average was designated as the half-life ($t_{1/2}$).

| Oligonucleotide sequence | | $t_{1/2}$ (seconds) |
|---|---|---|
| 5'-GTTTTTTTTTTTC-3' (natural type) | (SEQ ID NO: 10) | 260 |
| 5'-GTTTTTTTTT-XX-C-3' (X2) | (SEQ ID NO: 11) | 850 |

Figure 2:
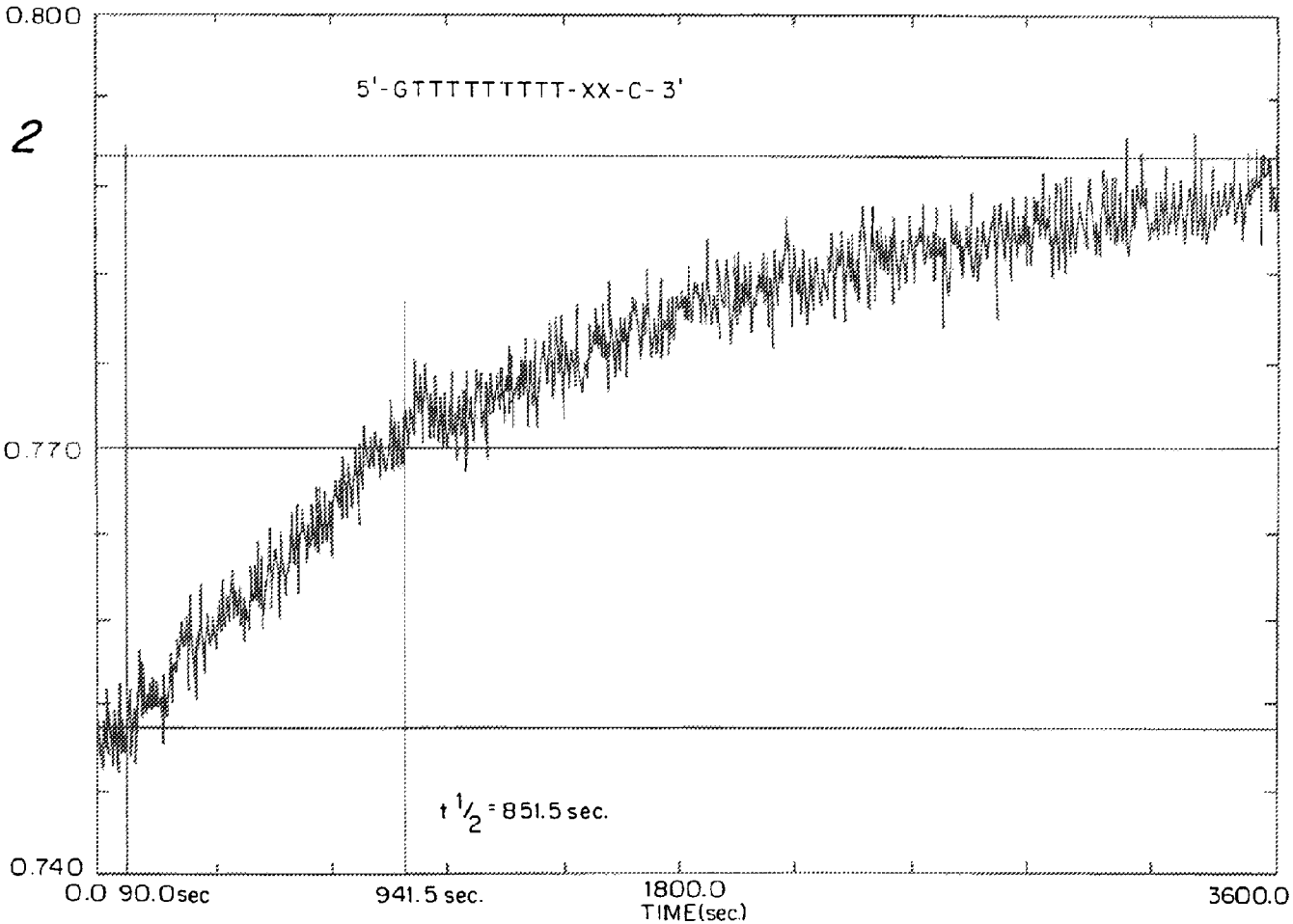
FIG. 2 is a chart showing the time course of the ultraviolet absorption (260 nm) of an oligonucleotide of the present invention (X2) decomposed with an exonuclease.

Charts showing the time course of the ultraviolet absorption are presented as FIG. 1 (natural strand) and FIG. 2 (X2). The ultraviolet absorption reached a plateau in about 30 minutes for the natural strand, and about 90 minutes for X2, after initiation of the enzyme reaction.

INDUSTRIAL APPLICABILITY

The use of this analogue provides an oligonucleotide analogue antisense molecule, which is minimally hydrolyzable with an enzyme in vivo, has a high sense strand binding ability, and is easily synthesized.

SEQUENCE LISTING

```
<160> NUMBER OF SEQ ID NOS: 12

<210> SEQ ID NO 1
<211> LENGTH: 12
<212> TYPE: DNA
<213> ORGANISM: synthetic construct

<400> SEQUENCE: 1

gcgtttttg ct                                                    12


<210> SEQ ID NO 2
<211> LENGTH: 12
<212> TYPE: DNA
<213> ORGANISM: synthetic construct
<220> FEATURE:
<221> NAME/KEY: misc_feature
<223> OTHER INFORMATION: n at position 4 is unknown
```

<400> SEQUENCE: 2 gcgnttttttg ct 12

<210> SEQ ID NO 3
<211> LENGTH: 12
<212> TYPE: DNA
<213> ORGANISM: synthetic construct
<220> FEATURE:
<221> NAME/KEY: misc_feature
<223> OTHER INFORMATION: n at position 6 is unknown

<400> SEQUENCE: 3 gcgttntttg ct 12

<210> SEQ ID NO 4
<211> LENGTH: 12
<212> TYPE: DNA
<213> ORGANISM: synthetic construct
<220> FEATURE:
<221> NAME/KEY: misc_feature
<223> OTHER INFORMATION: n at position 7 is unknown

<400> SEQUENCE: 4 gcgtttnttg ct 12

<210> SEQ ID NO 5
<211> LENGTH: 12
<212> TYPE: DNA
<213> ORGANISM: synthetic construct
<220> FEATURE:
<221> NAME/KEY: misc_feature
<223> OTHER INFORMATION: n at position 9 is unknown

<400> SEQUENCE: 5 gcgtttttng ct 12

<210> SEQ ID NO 6
<211> LENGTH: 12
<212> TYPE: DNA
<213> ORGANISM: synthetic construct
<220> FEATURE:
<221> NAME/KEY: misc_feature
<223> OTHER INFORMATION: n at positions 4 and 5 is unknown

<400> SEQUENCE: 6 gcgnnttttg ct 12

<210> SEQ ID NO 7
<211> LENGTH: 12
<212> TYPE: DNA
<213> ORGANISM: synthetic construct
<220> FEATURE:
<221> NAME/KEY: misc_feature
<223> OTHER INFORMATION: n at positions 6 and 7 is unknown

<400> SEQUENCE: 7 gcgttnnttg ct 12

<210> SEQ ID NO 8
<211> LENGTH: 12
<212> TYPE: DNA
<213> ORGANISM: synthetic construct
<220> FEATURE:
<221> NAME/KEY: misc_feature
<223> OTHER INFORMATION: n at positions 8 and 9 is unknown

<400> SEQUENCE: 8 gcgttttnng ct 12

<210> SEQ ID NO 9
<211> LENGTH: 12
<212> TYPE: DNA
<213> ORGANISM: synthetic construct
<220> FEATURE:
<221> NAME/KEY: misc_feature
<223> OTHER INFORMATION: n at positions 4-9 is unknown

<400> SEQUENCE: 9 gcgnnnnnng ct 12

<210> SEQ ID NO 10
<211> LENGTH: 13
<212> TYPE: DNA
<213> ORGANISM: synthetic construct

<400> SEQUENCE: 10 gtttttttt ttc 13

<210> SEQ ID NO 11
<211> LENGTH: 13
<212> TYPE: DNA
<213> ORGANISM: synthetic construct
<220> FEATURE:
<221> NAME/KEY: misc_feature
<223> OTHER INFORMATION: n at positions 11 and 12 is unknown

<400> SEQUENCE: 11 gtttttttt nnc 13

<210> SEQ ID NO 12
<211> LENGTH: 12
<212> TYPE: DNA
<213> ORGANISM: synthetic construct

<400> SEQUENCE: 12 agcaaaaaac gc 12

What is claimed is:

1. A nucleoside analogue of the following formula (I)

(I)

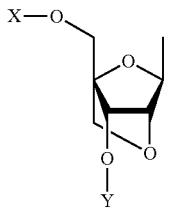

*or an amidite derivative thereof;* where B is a pyrimidine or purine nucleic acid base, and X and Y are identical or different, and each represents a hydrogen atom, an alkyl group, an alkenyl group, an alkynyl group, a cycloalkyl group, an aralkyl group, an aryl group, an acyl group, or a silyl group[, or an amidite derivative thereof].

2. A nucleoside analogue as claimed in claim 1, wherein X and Y each represents a hydrogen atom.

3. A mononucleoside amidite derivative as claimed in claim 1, wherein X is 4,4-dimethoxytrityl (DMTr), and Y is a 2-cyanoethoxy(diisopropylamino)phosphano group.

4. An oligonucleotide or polynucleotide analogue having one or more structures or the formula (Ia)

(Ia)

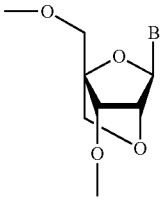

where B is a pyrimidine or purine nucleic acid base.

5. An oligonucleotide or polynucleotide analogue of the formula (II)

(II)

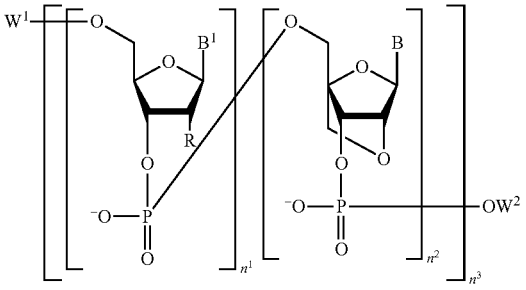

where $B^1$ and B are identical or different, and each Represents a pyrimidine or purine nucleic acid base, R is a hydrogen atom, a hydroxyl group, a halogen atom, or an alkoxy group, $W^1$ and $W^2$ are identical or different, and each represents a hydrogen atom, an alkyl group, an alkenyl group, an alkynyl group, a cycloalkyl group, an aralkyl group, an aryl group, an acyl group, a silyl group, a phosphoric acid residue, a naturally occurring nucleoside or a synthetic nucleoside bound via a phosphodiester bond, or an oligonucleotide or polynucleotide containing the nucleoside, $n^1$ or $n^2$ are identical or different, and each denotes an integer of 0 to 50, provided that $n^1$ and $n^2$ are not both zero, and that not all of the $n^2$ are zero at the same time, $n^3$ denotes an integer of 1 to 50, provided that when $n^1$ and/or $n^2$ are or is 2 or more, $B^1$ and B need not be identical, and R need not be identical.

6. The nucleoside analogue according to claim 1 wherein the amidite derivative is a phosphoramidite.

7. The nucleoside analogue according to claim 4 wherein the amidite derivative is a phosphoramidite.

8. The nucleoside analogue according to claim 5 wherein the amidite derivative is a phosphoramidite.

*9. The nucleoside analogue according to claim 1, which is purified.*

*10. The nucleoside analogue according to claim 1, wherein the nucleic acid base is cytosine, thymine, adenine, guanine, or a derivative thereof.*

*11. The oligonucleotide or polynucleotide analogue of claim 4, wherein the one or more structures of formula (Ia) are present at two or more locations and separated from each other by one or more naturally occurring nucleotides.*

*12. The oligonucleotide or polynucleotide analogue of claim 4, which has a length of 2 to 50 nucleotide and nucleotide analogue units.*

*13. The oligonucleotide or polynucleotide analogue of claim 4, which has a length of 10 to 30 nucleotide and nucleotide analogue units.*

*14. The oligonucleotide or polynucleotide analogue of claim 4, wherein the melting temperature of said oligonucleotide or polynucleotide analogue bound to a complementary DNA strand is at least about 2° C. greater than the melting temperature of a corresponding oligonucleotide or polynucleotide containing naturally occurring nucleotides in a 100 mM NaCl, 10 mM phosphate buffer (pH 7.2) solution.*

*15. The oligonucleotide or polynucleotide analogue of claim 4, wherein the melting temperature of said oligonucleotide or polynucleotide analogue bound to a complementary RNA strand is at least about 4° C. greater than the melting temperature of a corresponding oligonucleotide or polynucleotide containing naturally occurring nucleotides in a 100 mM NaCl, 10 mM phosphate buffer (pH 7.2) solution.*

*16. The oligonucleotide or polynucleotide analogue of claim 4, wherein the nucleic acid base is cytosine, thymine, adenine, guanine, or a derivative thereof.*

*17. A pharmaceutical composition comprising the oligonucleotide or polynucleotide analogue of any of claims 4 or 5.*

*18. The pharmaceutical composition of claim 17, further comprising one or more buffers, stabilizers, pharmaceutical carriers, or combinations thereof.*

*19. The pharmaceutical composition of claim 17, in the form of a parenteral, liposomal, or topical preparation.*

*20. The pharmaceutical composition of claim 17, wherein the oligonucleotide or polynucleotide analogue has a length of 2 to 50 nucleotide and nucleotide analogue units.*

*21. The pharmaceutical composition of claim 17, wherein the oligonucleotide or polynucleotide analogue has a length of 10 to 30 nucleotide and nucleotide analogue units.*

*22. The pharmaceutical composition of claim 17, wherein the oligonucleotide or polynucleotide analogue inhibits transcription of messenger RNA.*

*23. The pharmaceutical composition of claim 17, wherein the oligonucleotide or polynucleotide analogue inhibits the biosynthesis of a potentially pathogenic protein.*

*24. The pharmaceutical composition of claim 17, wherein the oligonucleotide or polynucleotide analogue suppresses the proliferation of an infectious virus.*

*25. A product comprising DNA or RNA annealed to the oligonucleotide or polynucleotide analogue of claim 4 or claim 5.*

*26. The product of claim 25, wherein said product is formed in vivo.*

*27. The product of claim 25, which comprises DNA.*

*28. The product of claim 25, which comprises RNA.*

*29. A method of increasing the melting temperature of an annealing product between a natural DNA or RNA-based sense strand and an antisense strand, comprising (a) incorporating into the antisense strand one of more structures of the formula (Ia) of claim 4; and (b) contacting said oligonucleotide or polynucleotide analogue with said complementary DNA or RNA.*

*30. The method of claim 29, wherein the melting temperature of the oligonucleotide or polynucleotide analogue for the complementary DNA is increased at least about 2° C. compared to the melting temperature of a corresponding oligonucleotide or polynucleotide containing naturally occurring nucleotides in a 100 mM NaCl, 10 mM phosphate buffer (pH 7.2) solution.*

*31. The method of claim 29, wherein the melting temperature of the oligonucleotide or polynucleotide analogue for the complementary RNA is increased at least about 4° C. compared to the melting temperature of a corresponding oligonucleotide or polynucleotide containing naturally occurring nucleotides in a 100 mM NaCl, 10 mM phosphate buffer (pH 7.2) solution.*

*32. The nucleoside analog according to claim 1, wherein and X and Y are identical or different, and each represents a hydrogen atom, an alkyl group, an alkenyl group, an alkynyl group, a cycloalkyl group, an aryl group, an acyl group, or a silyl group.*

* * * * *